US007933721B2

(12) United States Patent
Johnson et al.

(10) Patent No.: US 7,933,721 B2
(45) Date of Patent: Apr. 26, 2011

(54) MULTIPLEXED ANALYSIS FOR DETERMINING A SERODIAGNOSIS OF VIRAL INFECTION

(75) Inventors: Alison Jane Johnson, Fort Collins, CO (US); Bradley John Biggerstaff, Fort Collins, CO (US)

(73) Assignee: The United States of America as represented by the Department of Health and Human Services, Centers for Disease Control and Prevention, Washington, DC (US)

( * ) Notice: Subject to any disclaimer, the term of this patent is extended or adjusted under 35 U.S.C. 154(b) by 643 days.

(21) Appl. No.: 11/336,639

(22) Filed: Jan. 20, 2006

(65) Prior Publication Data

US 2006/0188982 A1    Aug. 24, 2006

Related U.S. Application Data

(60) Provisional application No. 60/645,768, filed on Jan. 20, 2005.

(51) Int. Cl.
*G01N 33/50* (2006.01)
(52) U.S. Cl. ........... 702/19; 435/7.1; 436/501; 436/507; 436/546; 705/32; 705/189
(58) Field of Classification Search ........................ None
See application file for complete search history.

(56) References Cited

U.S. PATENT DOCUMENTS

| | | | |
|---|---|---|---|
| 5,981,180 A | 11/1999 | Chandler et al. | |
| 6,046,807 A | 4/2000 | Chandler | |
| 6,139,800 A | 10/2000 | Chandler | |
| 6,268,222 B1 | 7/2001 | Chandler et al. | |
| 6,366,354 B1 | 4/2002 | Chandler | |
| 6,449,562 B1 | 9/2002 | Chandler et al. | |
| 6,514,295 B1 | 2/2003 | Chandler et al. | |
| 6,524,793 B1 | 2/2003 | Chandler et al. | |
| 6,592,822 B1 | 7/2003 | Chandler | |
| 6,599,331 B2 | 7/2003 | Chandler et al. | |
| 6,632,526 B1 | 10/2003 | Chandler | |
| 6,649,414 B1 | 11/2003 | Chandler et al. | |
| 6,696,304 B1 | 2/2004 | Davies | |

(Continued)

OTHER PUBLICATIONS

Blitvich et al., "Epitope-Blocking Enzyme-Linked Immunosorbent Assays for the Detection of Serum Antibodies to West Nile Virus in Multiple Avian Species", 2003, Journal of Clinical Microbiology, pp. 1041-1047.*

(Continued)

*Primary Examiner* — Carolyn L. Smith
(74) *Attorney, Agent, or Firm* — Klarquist Sparkman, LLP

(57) ABSTRACT

Clinical samples can be analyzed using microparticles to determine the serodiagnosis of a viral infection from two candidate viral infections of the same viral group. Serodiagnosis can be determined via a pooled population of subsets of microparticles, with the particles in the pooled population having a bound viral group-reactive antibody and the particles in each subset having at least one characteristic classification parameter that distinguishes between subsets. Viral antigens of antibodies of interest in the same viral-class as the viral group-reactive antibody can be bound to the viral group-reactive antibody on the microparticles, and subsequently exposed to a clinical sample. Binding and labeling can be used. Automated analysis of data from multiplexed flow analysis can determine the presence or absence of antibodies of interest in the sample, thereby diagnosing for two candidate viral infections in a single assay.

43 Claims, 14 Drawing Sheets

U.S. PATENT DOCUMENTS

| | | | |
|---|---|---|---|
| 6,773,812 | B2 | 8/2004 | Chandler et al. |
| 2002/0115062 | A1 | 8/2002 | Fletcher et al. |
| 2002/0172937 | A1 | 11/2002 | Dave et al. |
| 2003/0219803 | A1 | 11/2003 | Jayasena et al. |
| 2003/0232397 | A1 | 12/2003 | Brown et al. |
| 2004/0009506 | A1 | 1/2004 | Stephan et al. |
| 2004/0197769 | A1* | 10/2004 | Wong et al. .......... 435/5 |
| 2004/0208350 | A1 | 10/2004 | Rea et al. |
| 2004/0219517 | A1 | 11/2004 | Ecker et al. |

OTHER PUBLICATIONS

"Antibody," Wikipedia, http://en.wikipedia.org/wki/Antibody, 5 pages, webpage visited on Jan. 11, 2006.

Clarke et al., "Techniques for Hemagglutination and Hemagglutination-Inhibition with Arthropod-Borne Viruses," *American Journal of Tropical Medicine and Hygiene*, vol. 7, No. 5, pp. 561-573, Sep. 1958.

Davis et al., "West Nile Virus Recombinant DNA Vaccine Protects Mouse and Horse from Virus Challenge and Expresses in Vitro a Noninfectious Recombinant Antigen That Can Be Used in Enzyme-Linked Immunosorbent Assays," *Journal of Virology*, vol. 75, No. 9, pp. 4040-4047, May 2001.

Dreiseitl et al., "Comparing Three-class Diagnostic Tests by Three-way ROC Analysis," *Medical Decision Making*, vol. 20, No. 3, pp. 323-331, Jul.-Sep. 2000.

Earley et al., "Report From a Workshop on Multianalyte Microsphere Assays," *Cytometry (Clinical Cytometry)*, vol. 50, pp. 239-242, 2002.

Huhn et al., "West Nile Virus in the United States: An Update on an Emerging Infectious Disease," *American Family Physician*, vol. 68, No. 4, pp. 653-660, Aug. 15, 2003.

Johnson et al., "Detection of Anti-Arboviral Immunoglobulin G by Using a Monoclonal Antibody-Based Capture Enzyme-Linked Immunosorbent Assay," *Journal of Clinical Microbiology*, vol. 38, No. 5, pp. 1827-1831, May 2000.

Johnson et al., "Duplex Microsphere-Based Immunoassay for Detection of Anti-West Nile Virus and Anti-St. Lois Encephalitis Virus Immunoglobulin M Antibodies," *Clinical and Diagnostic Laboratory Immunology*, vol. 12, No. 5, pp. 566-574, May 2005.

Kellar et al., "Multiplexed Fluorescent Bead-Based Immunoassays for Quantitation of Human Cytokines in Serum and Culture Supernatants," *Cytometry*, vol. 45, pp. 27-36, 2001.

Lindsey et al., "Serum Dilution Neutralization Test for California Group Virus Identification and Serology," *American Society for Biology*, vol. 4, No. 6, pp. 503-510, 1976.

Martin et al., "Standardization of Immunoglobulin M Capture Enzyme-Linked Immunosorbent Assays for Routine Diagnosis of Arboviral Infections," *Journal of Clinical Microbiology*, vol. 38, No. 5, pp. 1823-1826, May 2000.

Monath et al., "Immunoglobulin M Antibody Capture Enzyme-Linked Immunosorbent Assay for Diagnosis of St. Louis Encephalitis," *Journal of Clinical Microbiology*, vol. 20, No. 4, pp. 784-790, Oct. 1984.

Mossman, "Three-way ROCs," *Medical Decision Making*, vol. 19, No. 1, pp. 78-89, Jan.-Mar. 1999.

Mostashari et al., "Epidemic West Nile encephalitis, New York, 1999: results of a household-based seroepidemiological survey," *The Lancet*, vol. 358, pp. 261-264, Jul. 2001.

Tardei et al., "Evaluation of Immunoglobulin M (IgM) and IgG Enzyme Immunoassays in Serologic Diagnosis of West Nile Virus Infections," *Journal of Clinical Microbiology*, vol. 38, No. 6, pp. 2232-2239, Jun. 2000.

Wong et al., "Detection of Human Anti-Flavivirus Antibodies with a West Nile Virus Recombinant Antigen Microsphere Immunoassay," *Journal of Clinical Microbiology*, vol. 42, No. 1, pp. 65-72, Jan. 2004.

Wong et al., "Immunoassay Targeting Nonstructural Protein 5 to Differentiate West Nile Virus Infection from Dengue and St. Louis Encephalitis Virus Infections and from Flavivirus Vaccination," *Journal of Clinical Microbiology*, vol. 41, No. 9, pp. 4217-4223, Sep. 2003.

Jones et al., "Multiplex Assay for Detection of Strain-Specific Antibodies Against the Two Variable Regions of the G Protein of Respiratory Syncytial Virus," *Clinical and Diagnostic Laboratory Immunology*, May 2002, (pp. 633-638).

Martins, "Development of Internal Controls for the Luminex Instrument as Part of a Multiplex Seven-Analyte Viral Respiratory Antibody Profile," *Clinical and Diagnostic Laboratory Immunology*, Jan. 2002, (pp. 41-45).

Opalka et al., "Simultaneous Quantitation of Antibodies to Neutralizing Epitopes on Virus-Like Particles for Human Papillomavirus Types 6, 11, 16 and 18 by a Multiplexed Luminex Assay," *Clinical and Diagnostic Laboratory Immunology*, Jan. 2003, (pp. 108-115).

Yan et al., "Microsphere-base duplexed immunoassay for influenza virus typing by flow cytometry," *Elsevier Journal of Immunology Methods*, 2004, (pp. 27-38).

"Smaller Reagent Manufacturers Provide Their own Answers to Reagent Rental Contracts with New Ways to Cut Costs in the Clinical Laboratory Space," *Business Wire*, 2 pages, Feb. 2004.

"U.S. Clinical Chemistry and Immunoassay Reagents Markets," Frost & Sullivan, http://www.mindbranch.com/listing/product/R1-4176.html, 6 pages, Feb. 2004.

Johnson et al., "Duplex Microsphere-Based Immunoassay for Detection of Ant-West Nile Virus and Anti-St. Louis Encephalitis Virus Immunoglobin M Antibodies," *Clinical and Diagnostic Laboratory Immunology*, vol. 12, No. 5, p. 566-574, May 2005.

Wong et al., "Immunoassay Targeting Nonstructural Protein 5 to Differentiate West Nile Virus Infection from Dengue and St. Louis Encephalitis Virus Infections and from Flavivirus Vaccination," *Journal of Clinical Microbiology*, pp. 4217-4223, Sep. 2003.

"A Microsphere Immunofluorescence Assay which measures specific Virus Nonstructural Proteins in sera and spinal fluids," Health Research, http://www.hrinet.org/techtran/technologies/westnile.htm, 2 pages, dated at least as early as Nov. 29, 2004.

"APHL," Association of Public Health Laboratories, http://web.archive.org/web/20041128092409/http://www.aphl.org, 2 pages, web-archived on Nov. 28, 2004.

"Bayer Diagnostics—About Us," Bayer HealthCare, http://web.archive.org/web/20040722015028/http://www.bayerdiag.com/aboutus.cfm, 1 page, web-archived on Jun. 6, 2004.

"Bioterrorism Detection," Biohazard News, http://web.archive.org/web/20041012194128/http://biohazardnews.net/int_radvak.shtml, 6 pages, Jun. 3, 2003.

"Focus On West Nile Virus Diagnostic Tests," Focus Technologies, http://web.archive.org/web/20041114235146/http://www.focustechnologies.com/cms/cms.asp?cms_220QNMSEU, 1 page, web-archived on Nov. 14, 2004.

"Immunoassay Standardization: Is It Possible, Who Is Responsible, Who Is Capable?" *Clinical Chemistry* 47, No. 5, pp. 815-820, 2001.

"Orchard Software Corporation: Specialists in Laboratory Information Systems (LIS)," Orchard Software Corporation, http://web.archive.org/web/20041107093844/http://orchardsoft.com, 3 pages web-archived on Nov. 7, 2004.

"Panbio :: Welcome," http://www.panbio.com.au/, 2 pages webpage accessed on Dec. 8, 2004.

"Panbio Overview," Panbio Innovative Diagnostic Solutions, 26 pages, Jul. 2004.

"Products: The FastPack® System," Qualigen Inc., http://web.archive.org/web/20041010035332/http://www.qualigeninc.com/products.htm, 1 page, web-archived on Oct. 10, 2004.

"Quantitative Testing," College of American Pathologists, http://web.archive.org/web/20050313115711/http://www.cap.org/apps/docs/committees/pointofcare/poc_quantitativetesting.html, 6 pages, web-archived on Mar. 13, 2005.

"Solutions/Reference Labs," Broadlane.com, http://web.archive.org/web/20041018222557/http://www.broadlane.com/cus/cus_7.html, 2 pages, web-archived on Oct. 18, 2004.

"Test Format Descriptions," Sierra Resources International, http://web.archive.org/web/20041116085337/http://www.sierraresources.com/test.htm, 3 pages, web-archived on Nov. 16, 2004.

"VecTest West Nile/St. Louis Encephalitis Virus Assay," Medical Analysis System, Inc., http://web.archive.org/web/20041018235819/http://mas-inc.com/products/Vectest.htm, 1 page, web-archived on Oct. 18, 2004.

"Welcome to Focus Technologies," Focus Technologies, http://web.archive.org/web/20041104013355/http://www.focustechnologies.com/0-home/index.asp, 1 page, web-archived on Nov. 4, 2004.

Bangs et al., "Microspheres, Part 1: Selection, Cleaning, and Characterization,"*IVD Technology Magazine*, 12 pages, http://web.archive.org/web/20041015022318/http://www.devicelink.com.ivdt/archive/95/03/009.html, Mar. 1995.

Kramer, "Testing of Field Specimens for West Nile and Other Arboviruses," Arbovirus Laboratory, Wadsworth Center, New York State Department of Health, 50 pages, 2002.

Ripley, *Pattern Recognition and Neural Networks*, Cambridge University Press, pp. 17-39, 69-71, and 91-105, 1996.

Roehrig et al., "Identification of Epitopes on the E. Glycoprotein of Saint Louis Encephalitis Virus Using Monoclonal Antibodies," *Virology*, 128, pp. 118-126, 1983.

Weingartl et al., "Comparison of assays for the detection of West Nile virus antibodies in chicken serum," Canadian Veterinary Medical Association, *Can J Vet Res.*, 67(2): 128-132, May 2003.

* cited by examiner

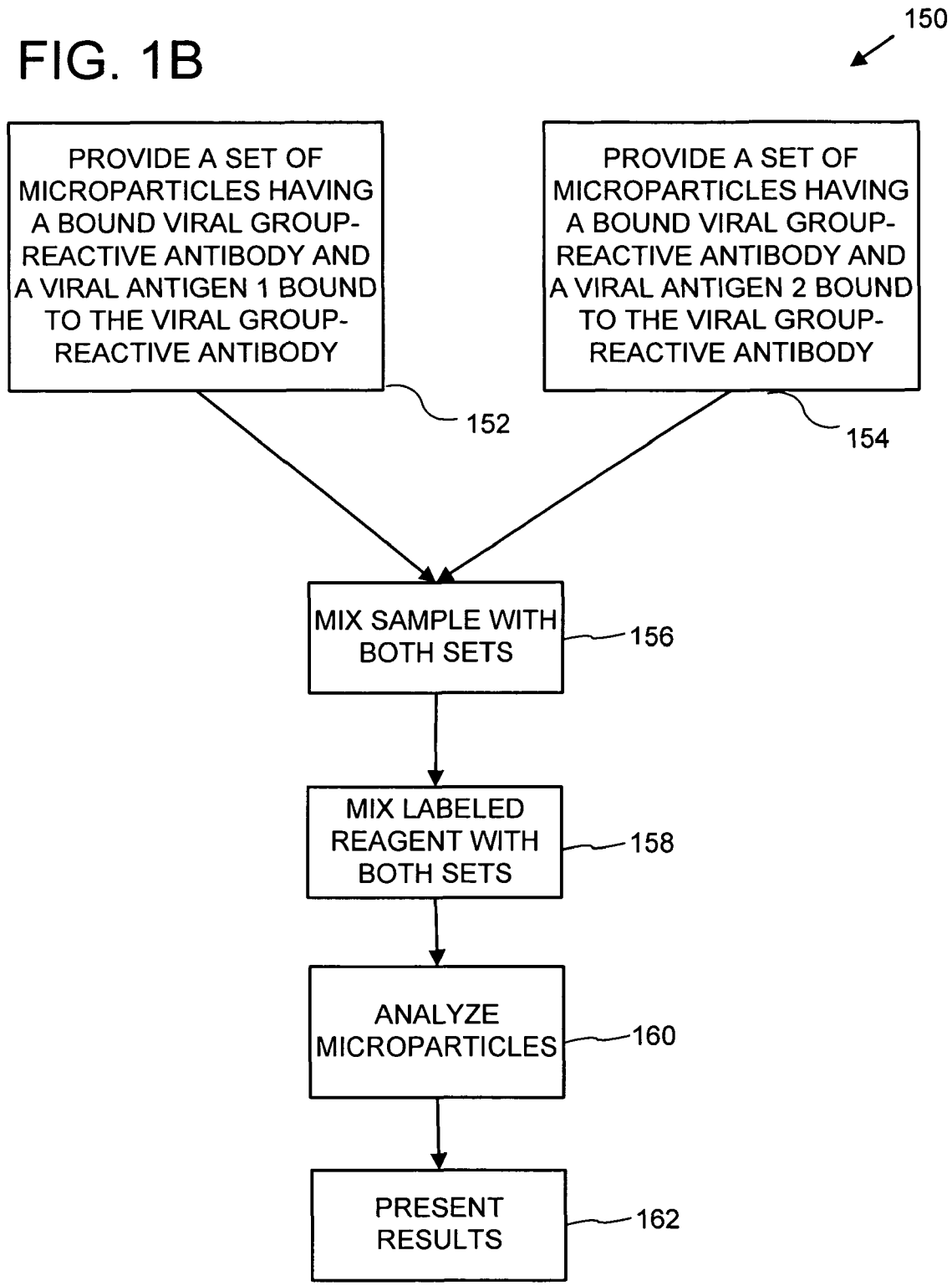

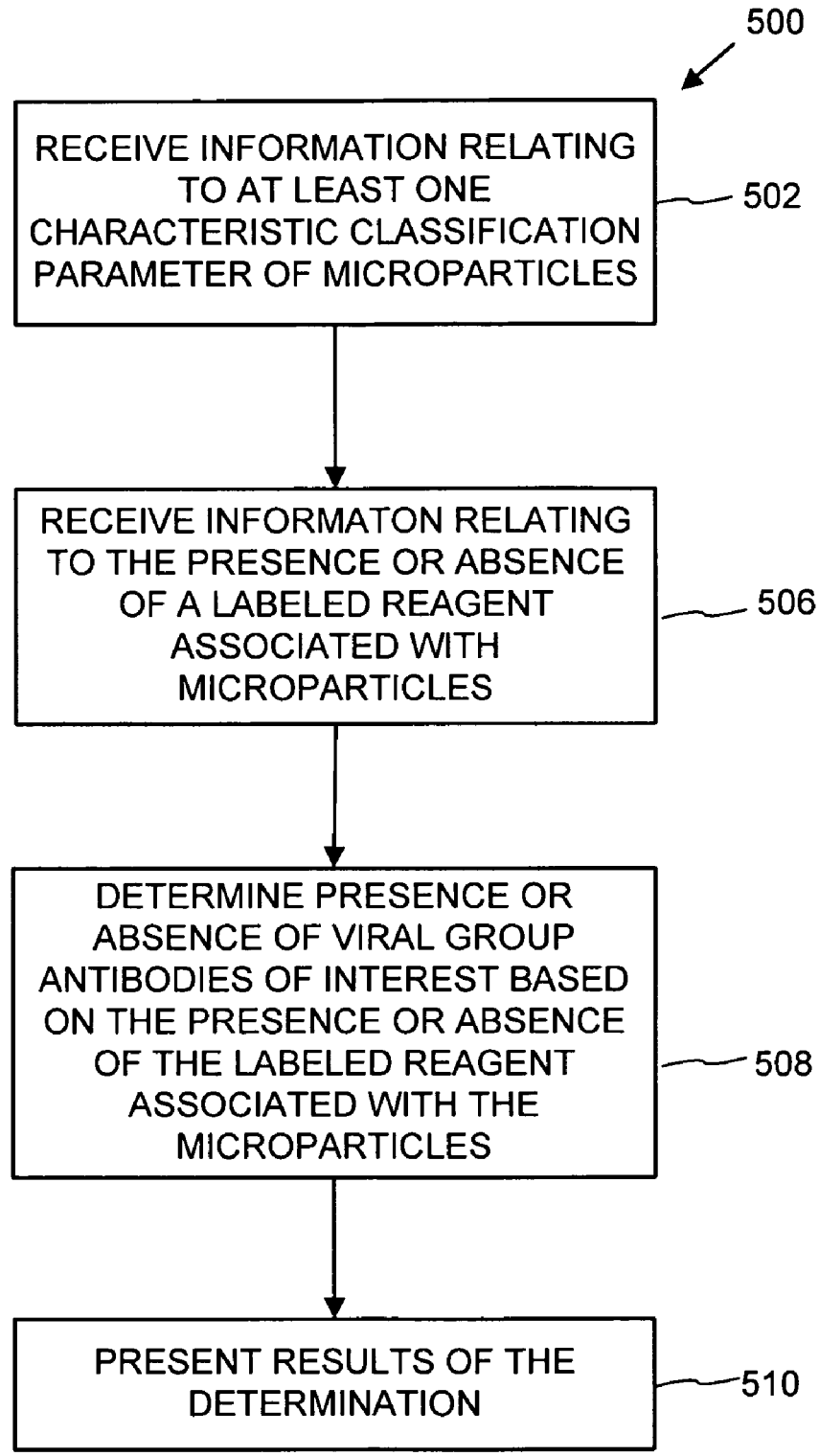

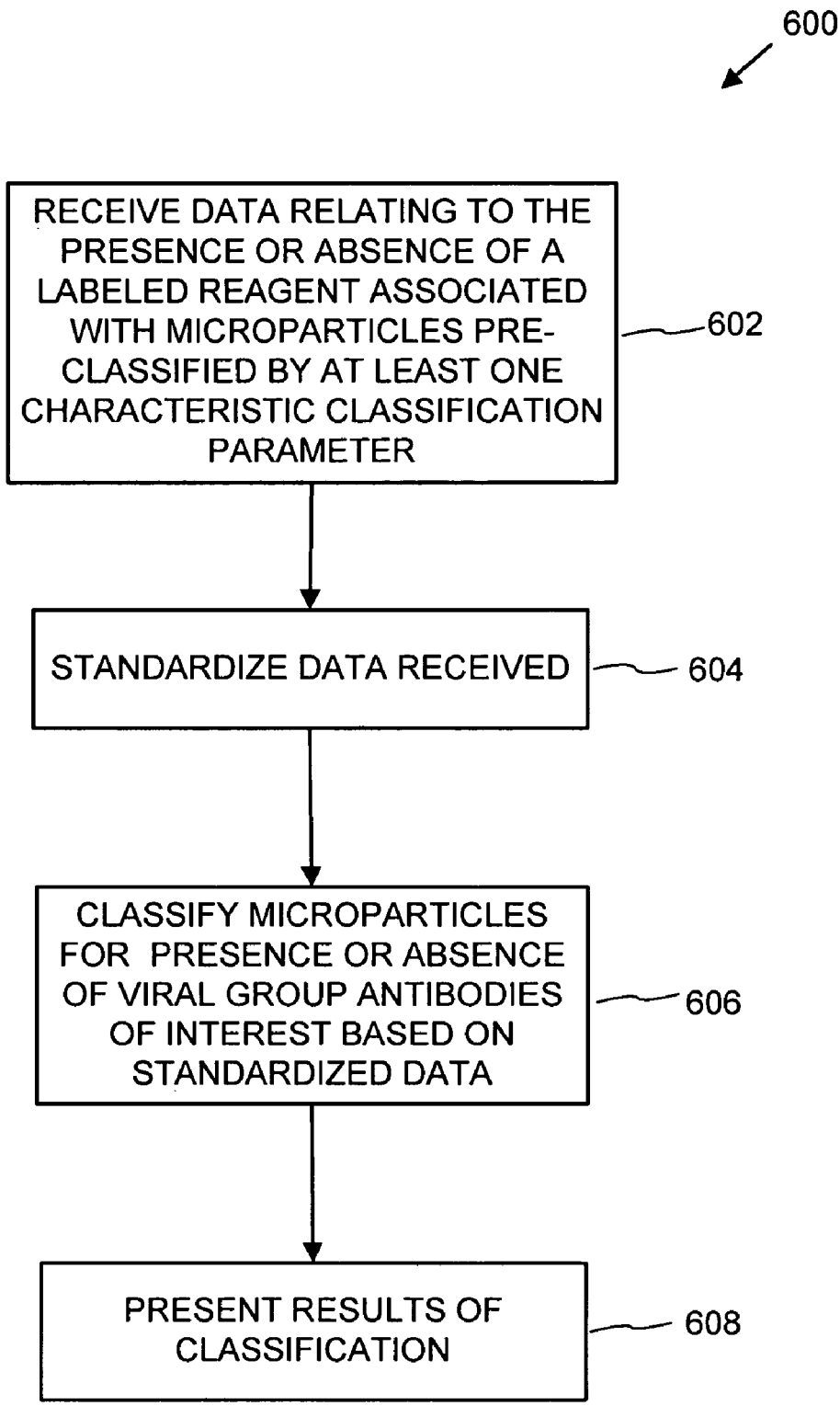

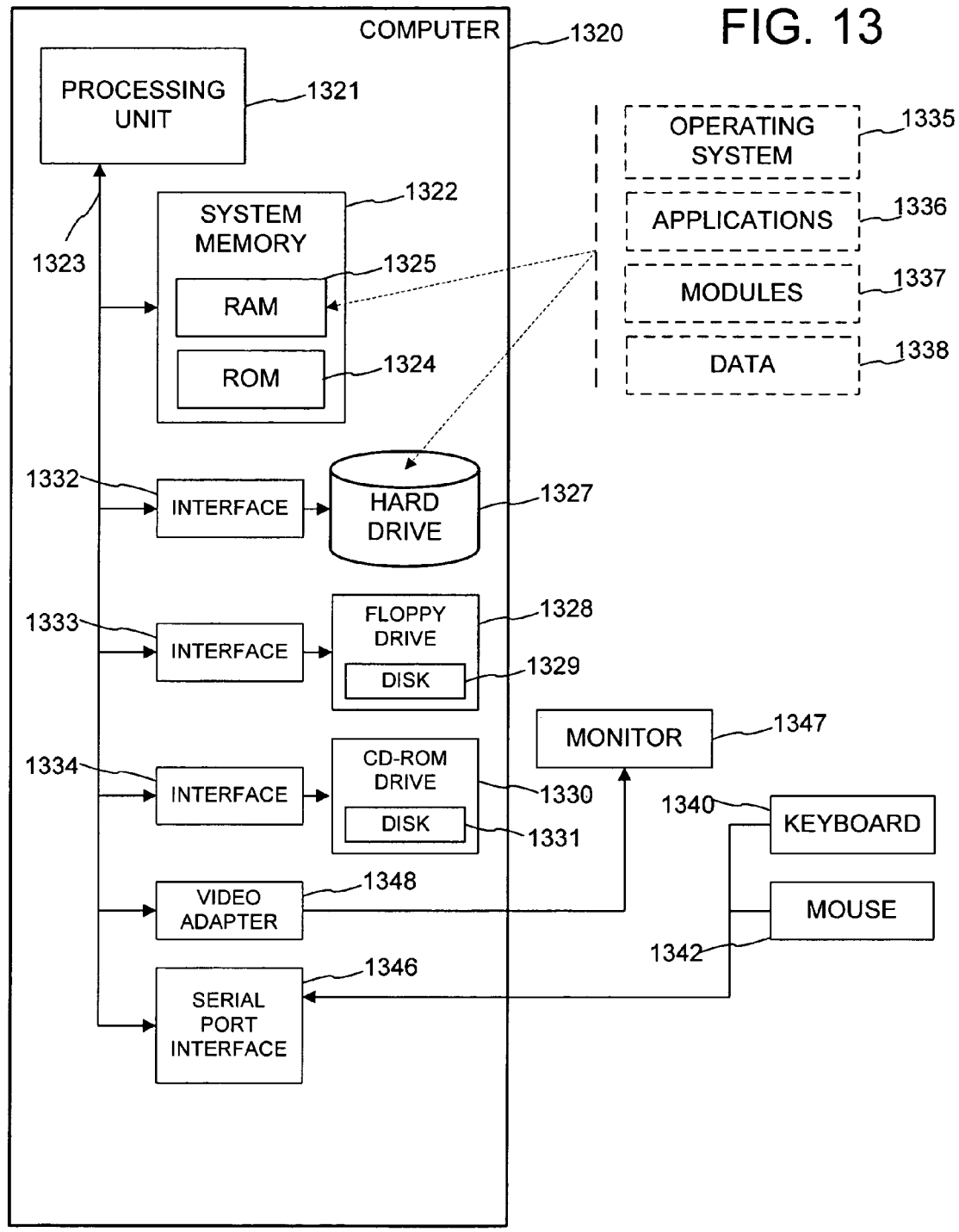

MULTIPLEXED ANALYSIS FOR DETERMINING A SERODIAGNOSIS OF VIRAL INFECTION

CROSS-REFERENCE TO RELATED APPLICATIONS

This application claims the benefit of U.S. Provisional Patent Application No. 60/645,768 to Johnson et al, filed Jan. 20, 2005, entitled, "MULTIPLEXED ANALYSIS FOR DETERMINING A SERODIAGNOSIS OF VIRAL INFECTION," which is hereby incorporated herein by reference.

REFERENCE TO COMPUTER PROGRAM LISTING APPENDIX

The present application includes a computer program listing appendix. The appendix contains an ASCII text file of the computer program listing as follows:
Filename: miaclassify.txt
Size: 29.4 kilobytes (30,174 bytes)
Date Created: Jan. 19, 2006 (CD Created Jan. 20, 2006)
The computer program listing appendix is hereby expressly incorporated by reference in the present application.

FIELD

The field relates to laboratory diagnostic analysis of clinical specimens.

BACKGROUND

Technology for the analysis of clinical specimens has provided significant advances in the field of medicine and public health. For example, it is now possible to routinely diagnose many clinical conditions using a wide variety of assays which determine qualitative and/or quantitative characteristics of a specimen. The methods of detecting multiple viral infections of the same viral group through a single assay have thus far shown only very limited capability and questionable results. A variety of reasons have been mentioned for these limitations, including the particularly difficult solution of standardizing an immunoassay for heterogeneous antigens. Additional reasons include the extended times typically required to enable the detection and classification of multiple viral infections of the same viral group, unwieldy collection, classification and analysis in the algorithms analyzing the data, and the inability to positively identify more than one viral infection in the same test. Previous multiple viral detection methods have been able to identify one viral infection and distinguish secondary viral infections by a process of elimination. A single assay able to efficiently and accurately positively detect a single viral infection from two candidate viral infections of the same viral group in a clinical sample would clearly be an improvement in the field. The capability to perform simultaneous, multiple determinations in a single assay process is known as "multiplexing" and the method of utilizing such determinations is "multiplexing analysis."

Microsphere "bead"-based (microparticle) immunoassays (MIAs) are becoming increasingly popular as a serological option for laboratory diagnosis of many diseases. The technology involves the detection and analysis of a reaction attached to microparticles. The common detecting instrument is a simplified flow cytometer, which has lasers that simultaneously identify the microparticle sets and measure the fluorescence associated with the reaction. Previous attempts have used microparticles coupled to recombinant envelope and nonstructural proteins, but such attempts cannot concurrently positively diagnose multiple viral infections of the same viral group in a single assay.

The more traditional serological method for identifying an infecting virus is the time-consuming and technically difficult plaque-reduction neutralization test (PRNT). The serological testing algorithm in common usage in the U.S. state health departments uses the immunoglobulin M (IgM) antibody capture enzyme-linked immunosorbent assay (MAC-ELISA) and the indirect immunoglobulin G (IgG) ELISA as primary tests following by confirmatory PRNT tests for positive samples from the ELISA testing. IgG antibodies to viruses within the same serocomplex exhibit extensive cross-reactivity, whereas IgM antibodies are less cross-reactive. The MAC-ELISA is a 2-day test that requires 4 hours of hands-on time for a 40-sample test. This combination of assays is highly sensitive and specific, but can require in total 2-3 days to complete, as overnight incubations are deemed necessary to enhance sensitivity. Thus, the advent of a more rapid, yet equally sensitive, single test to replace separate ELISA tests to detect a single viral infection from two candidate viral infections of the same viral group in a clinical sample would be a great benefit to addressing public health needs. Many viruses can be transmitted through blood transfusion and organ transplantation, further heightening the urgency and need for the development of specific and rapid serological assays of a single viral infection considered from viruses of the same viral group.

SUMMARY

The presence or absence of antibodies of interest within the same viral group in a clinical serum sample can be determined using a rapid and accurate multiplexed method. For example, anti-West Nile and anti-Saint Louis encephalitis IgM antibodies can be detected and differentiated from IgM antibody-negative serum samples using the described techniques. The described techniques can also be applied to antibodies to other viruses. Other antibody isotypes (e.g., IgG) can also be detected.

Results management for a duplex microparticle immunoassay technique can incorporate data manipulation and classification algorithms not previously applied to viral group serological determination techniques. For example, data from the microparticle immunoassay technique can be standardized and then classified via discriminant analysis to determine the presence or absence of antibodies of interest in the clinical sample tested. Furthermore, along with allowing for a single result to be generated, data manipulation and classification algorithms allow for the results to be compared back to the original large data sets used in development. In this way, results from different laboratories can now be directly compared to one another, providing that the same controls are used. Additionally, as described herein, the use of different antigen lots or different test performances among labs can be accounted for by data manipulation techniques.

The techniques described herein can be applied to any number of viral groups where determining positive identification of viral antibodies from the same viral group in a clinical sample in a single multiplexed test is desired.

Additional features and advantages of the technologies described herein will be made apparent from the following detailed description of illustrated embodiments, which proceed with reference to the accompanying drawings.

BRIEF DESCRIPTION OF THE DRAWINGS

FIG. 1B is a flowchart showing an exemplary method for determining the presence or absence of antibodies of interest in a sample with a set of microparticles to which a viral group-reactive antibody is covalently bound.

FIG. 5 is a flowchart showing an exemplary computer-implemented method for determining the presence or absence of antibodies of interest in a sample.

FIG. 6 is a flowchart showing an exemplary method for determining the presence or absence of viral group antibodies of interest based on the presence or absence of a labeled reagent associated with microparticles pre-classified by at least one characteristic classification parameter.

FIG. 13 is a block diagram of an exemplary computer system for implementing the described computer-implemented technologies.

DETAILED DESCRIPTION

Overview of Technologies

Figure 1A:
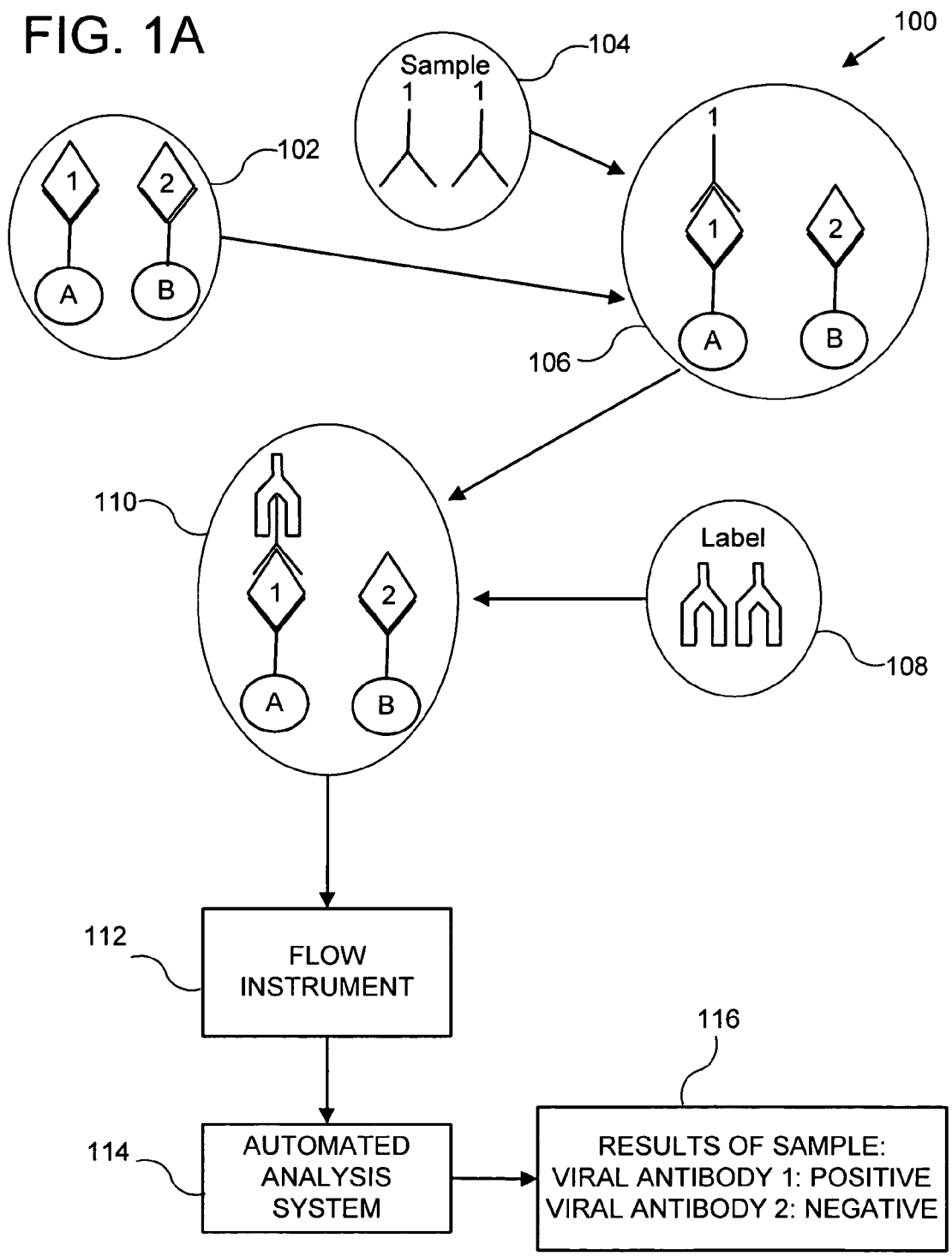
FIG. 1A is a block diagram of an exemplary system for determining the presence or absence of antibodies of interest in a sample with a set of microparticles to which a viral group-reactive antibody is covalently bound.

The technologies described herein can be used in any of a variety of scenarios in which identification of the presence or absence of antibodies of interest within the same viral group in a clinical serum sample is useful.

An antibody of interest includes any antibody in a clinical sample that is of interest. In practice, antibodies of interest include specific viral antibodies (e.g., antibodies for a particular virus type) in a sample that reflect current, recent, or historic viral infection. Antibodies of interest can include viral antibodies to a viral group.

A microparticle includes any microsphere, bead, or the like with a surface suitable for binding (e.g., suitable for binding an antibody), whether or not such surface has bound to a reactive particle. For example, a microparticle can be a multianalyte microsphere with a carboxylated surface. Man-made microspheres or beads for use in flow cytometry and flow instrumentation are generally well known in the art.

A reactive microparticle comprises any microparticle to which a reactive particle is bound. For example, a microparticle with a covalently bound antibody is a reactive microparticle.

A virus type or antigen type is sometimes referred to simply as a "virus" or "antigen" and indicates a particular species of virus. For example, West Nile virus and Saint Louis encephalitis virus are two different virus types.

A viral group-reactive antibody includes any antibody that is reactive to a plurality of viral antigens (e.g., for a plurality of virus types) within the same viral group. For example, a flavivirus group-reactive antibody such as the monoclonal antibody (MAb) 6B6C-1, dengue 4G2, or Murray Valley 4A1B-9 is reactive with arbovirus antigens within the flavivirus genus, which includes the West Nile virus, Saint Louis encephalitis virus, Japanese encephalitis virus, and dengue virus. Similarly, for example, an alphavirus group-reactive antibody such as eastern equine encephalitis (EEE) 1A4B-6 or WEE 2A2C-3 is reactive with alphavirus antigens within the alphavirus genus, which includes eastern equine encephalitis virus, western equine encephalitis virus, and Venezuelan equine encephalitis virus. Similarly, for example, a bunyavirus group-reactive antibody such as LAC 10G5.4 is reactive with bunyavirus antigens within the bunyavirus genus, which includes the California serogroup of bunyaviruses, which includes La Crosse virus.

A negative control antigen comprises any antigen that is reactive with an antibody of interest (or any reactive nonspecific proteins) and used as a control in an experimental study or assay to confirm reactivity between antigens and the antibody of interest. The negative control antigen is used to bind any antibody of interest or any reactive nonspecific proteins in a sample and the bound pair is expected to be washed away prior to analysis because the negative control antigen is not commonly bound to the antibody which is bound to the microparticle. Any bound pairs which happen to bind to any microparticles are commonly referred to as "background noise" in the experiment.

A characteristic classification parameter includes any measurable characteristic or property used as a parameter for classifying one type of microparticle from another type. Such parameters include microparticle size, microparticle color, microparticle fluorescence emission, and the like.

Positive control serum comprises serum in which known antibodies are present in the serum. A positive control serum can be used as a control in an experimental study or assay to confirm reactivity between antigens and the antibodies tested for in a sample. Reaction rates between specific viral antigens and the antibodies tested for in a sample can differ and the use of positive control serum allows for quantification of such differences for data standardization purposes.

Negative control serum comprises serum in which known antibodies are not present in the serum. A negative control serum can be used as a control in an experimental study or assay to confirm that other reactions are not affecting the experimental or assay results obtained on the samples. Any positive results of reactivity using a negative control serum would be cause for concern about the quality of the experimental or assay results.

A labeled reagent includes any composition that is labeled fluorescently or the like and is able to react with a desired composition so as to label the desired composition fluorescently or the like. For example, an antibody can be fluorescently labeled. Similarly, for example, an antibody can be attached to an enzyme such as alkaline phosphate, which can rapidly convert many molecules of an added colorless substrate into colored products, or nonabsorbent substrates into intensely absorbent products.

A flow instrument can include any instrument that analyzes particular particles in a fluid mixture based on the particles' characteristics. For example, microparticle fluorescence emission (determined via dyes encapsulated within beads) and fluorescence from labeled reagent can be simultaneously determined by a simplified flow cytometer instrument measuring a single microparticle at a time. Such an instrument can use dual lasers, with a first laser to determine a microparticle type via a particle's characteristic(s) and a second laser to determine if a particular labeled reagent is associated with the microparticle. Similarly, for example, a flow cytometer can be used to determine microparticle type based on size, and/or other flow instruments can be used to determine microparticle type based on color or the like.

Plates include any lab plates on which experiments or assays can be conducted. For example, a multi-well plate (e.g., a 96-well or other multi-well plate) in which biological and chemical reactions can occur in the plate wells can be used.

Example 1

Exemplary Samples

In any of the examples herein, a sample can include serum, CSF (cerebrospinal fluid), plasma or other substances from an animal (e.g., human) that include biomolecules and antibodies representative of those present in the animal. Samples can include processed blood samples, secretions and the like.

Example 2

Exemplary System for Determining the Presence or Absence of Antibodies of Interest in a Sample FIG. 1A shows an exemplary system 100 for determining the presence or absence of antibodies of interest in a sample with a set of microparticles to which a viral group-reactive antibody is covalently bound. The system can be used to perform a multiplexed detection of two or more antibodies of interest (e.g., to specific, different antigens) in a sample 104.

A set of microparticles (beads of type "A" and "B") 102 to which the same viral group-reactive antibodies are covalently bound (with specific viral antigens bound to the viral group-reactive antibodies in a bead-antibody-antigen complex) is mixed with sample 104 to test for the presence of antibodies of interest in sample 104. Label 108 is mixed with sample-exposed microparticles 106 to label microparticles bound with antibodies of interest 110 from the sample for detection by flow instrument 112. Automated analysis system 114 analyzes the flow instrument detection data to determine results 116 indicating the presence or absence of antibodies of interest in a sample.

The set of microparticles 102 have specific viral antigens (e.g., of different virus types) ("1" and "2") of the same viral group as the viral group-reactive antibody bound to the microparticles (e.g., a specific viral antigen is bound to the viral group-reactive antibody bound to the microparticle forming a specific bead type complex). As illustrated, bead type "A" has viral antigen "1" bound and bead type "B" has viral antigen "2" bound, however the alternative combination can be used. The same bead type can be used with the same antigen type in the system for consistency and accuracy. The viral antigens are also reactive with specific viral antibodies of interest in a sample (e.g., antigen type "1" is reactive with antibody of interest type "1" and antigen type "2" is reactive with antibody of interest type "2"). Some cross-reactions between antibodies can occur, however they can be accounted for during analysis.

In the example, sample 104 has antibodies of interest of type "1," but not type "2." Therefore, when the set of microparticles 102 are mixed with sample 104, antibodies of interest of type "1" bind to antigen type "1" bound to microparticles with bead type "A." The label 108 is illustrated as a fluorescently labeled antibody reactive with antibodies of interest type "1" and "2."

The flow instrument 112 can detect the bead type (and therefore the antigen type bound to the bead type, i.e., the bead-antibody-antigen complex) and also the associated label 108, if any The quantity of beads (e.g., and whether they are labeled) can be determined for further analysis.

The automated analysis system 114 can employ any combination of the technologies described herein to determine and output results 116 of sample 104. The results can be provided according to any of the techniques or formats described herein. For example, output can take a format other than that shown in the example of FIG. 1A.

Methods for administrating a bioactive composition to a subject are described in detail below.

Example 3

Exemplary Method for Determining the Presence or Absence of Antibodies of Interest in a Sample FIG. 1B shows an exemplary method 150 for determining the presence or absence of antibodies of interest in a sample with a set of microparticles to which a viral group-reactive antibody is covalently bound. The actions in method 150 can be performed by human or automated means.

At 152, a set of microparticles having a bound viral group-reactive antibody and a viral antigen "1" bound to the viral group-reactive antibody is provided. The set of microparticles 152 can be obtained from an outside source, prepared prior to use in the method and stored, or prepared as part of the method (e.g., as an initial action). The viral antigen "1" is a specific viral antigen of the same viral group as the viral group-reactive antibody bound to the microparticle and is reactive with a first specific viral antibody of interest in a sample.

At 154, another set of microparticles having the same bound viral group-reactive antibody as the set 152 and a viral antigen "2" (e.g., an antigen of a different virus type than that of antigen "1"). bound to the viral-group antibody is provided. The set of microparticles 154 can be obtained from an outside source, prepared prior to use in the method and stored, or prepared as part of the method as an initial action. The viral antigen "2" is a specific viral antigen of the same viral group as the viral group-reactive antibody bound to the microparticle and is reactive with a second specific viral antibody of interest in a sample.

At 156, a clinical serum sample is mixed with both sets to allow viral antibodies of interest in the clinical serum sample to react with either the viral antigens "1" or "2," therefore becoming bound to the microparticles.

At 158, a labeled reagent is mixed with both sets to bind with the viral antibodies of interest bound to viral antigens "1" and "2," thereby labeling the microparticles with bound antibodies of interest.

At 160, the microparticles are analyzed to determine those microparticles having viral antigens "1" and "2" and those microparticles having labeled microparticles (i.e., the microparticles with bound antibodies of interest).

At 162, the results of the analyzed particles are presented (e.g., the presence or absence of antibodies of interest in the clinical sample is presented via the determination of microparticles of type "1" or "2" being labeled microparticles). In any of the methods herein, it may be desirable to complete only a subset of method actions shown; for example, preparation of antibody coated microparticles for later use, analyzing microparticles and storing the data for later presentation, and the like. Additionally, it may be desirable for the actions to be performed by different actors.

Example 4

Exemplary Plate Assay

Figure 2:
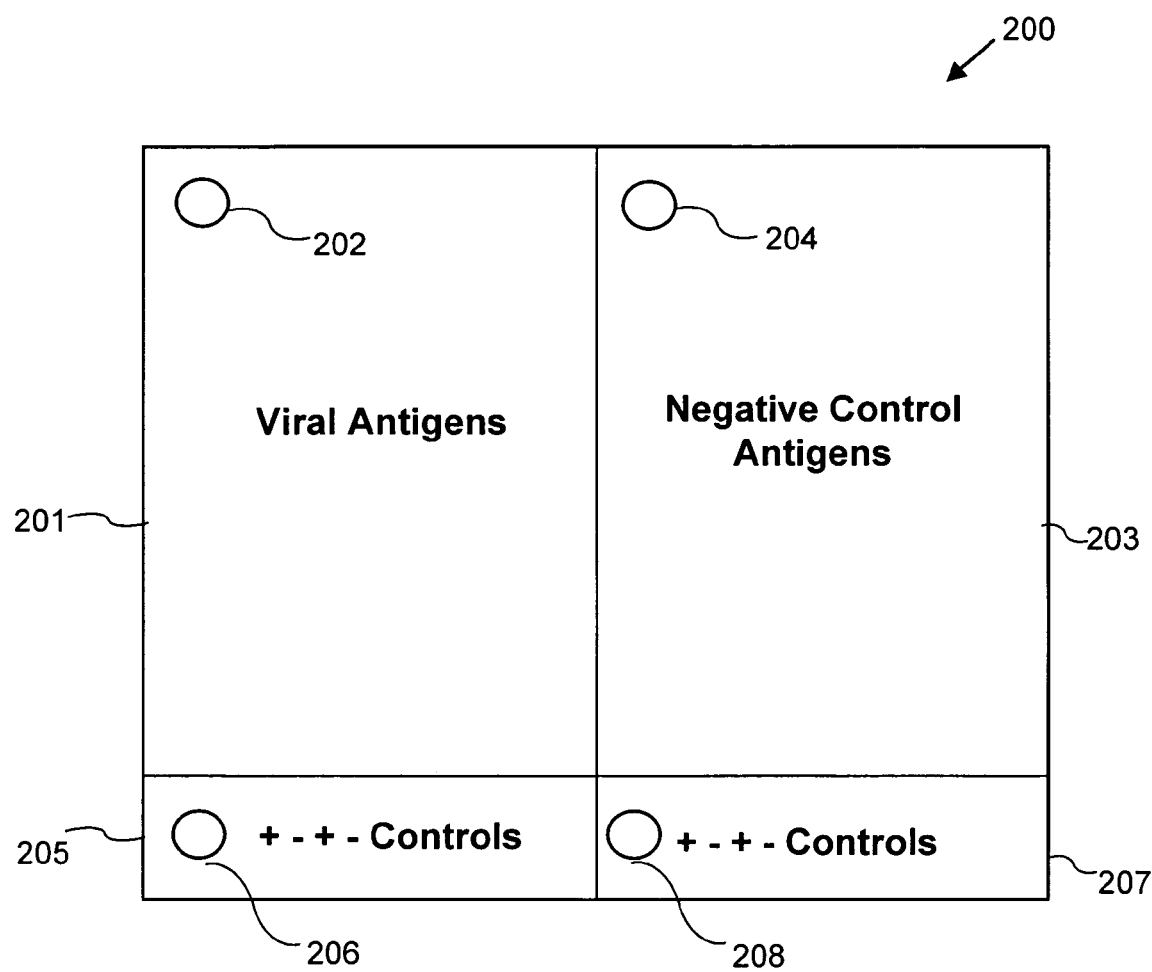
FIG. 2 illustrates an exemplary multi-well plate in which the reactions in the exemplary method for determining the presence or absence of antibodies of interest in a sample with a set of microparticles to which a viral group-reactive antibody is covalently bound can be implemented.

FIG. 2 shows an exemplary multi-well plate 200 in which the reactions in the exemplary method 150 for determining the presence or absence of antibodies of interest in a sample with a set of microparticles to which a viral group-reactive antibody is covalently bound can be implemented. In practice, a 96-well or other multi-well plate can be used. In the interest of brevity, all wells are not shown.

At 201, one half of the multi-well plate 200 is used for sets of microparticles having a bound viral group-reactive antibody and a viral antigen bound to the viral group-reactive antibody. Sets having different types of viral antigens (e.g., viral antigens "1" and "2" shown in FIG. 1A) are combined in wells 202, and sample serum is mixed with the sets in wells 202. Subsequently, a labeled reagent is mixed with the sets in wells 202, wherein if the serum does have antibodies of interest, the microparticles will be bound with a virus-group reactive antibody, a viral antigen will be bound to the viral group-reactive antibody, an antibody of interest will be bound to the viral antigen, and a labeled reagent will be bound to the antibody of interest. The presence of labeled reagent thus indicates presence of antibodies of interest. Washing steps can be included to ensure quality control.

At 203, the other half of the multi-well plate 200 is used for sets of microparticles having a bound viral group-reactive antibody and a negative control antigen pretreated on the microparticles. Sets having different types of negative control antigens are combined in wells 204, and sample serum is mixed with the sets in wells 204. Subsequently, a labeled reagent is mixed with the sets in wells 204, wherein if the serum does have antibodies of interest, the antibodies of interest will bind with the negative control antigen, and the labeled reagent will bind with the antibodies of interest. In a washing step, the antibodies of interest bound to the negative control antigen tend to be washed away because the negative control antigen is not commonly bound to the viral group-reactive antibody. In this way, wells 204 act as a negative control, and any labeled reagent detected by a flow instrument is background noise in the experiment or assay.

At 205, either positive or negative control serum is applied to select wells 206 containing sets of microparticles having a bound viral group-reactive antibody and a viral antigen bound to the viral group-reactive antibody. The wells in which positive control serum is applied result in microparticles having a bound viral group-reactive antibody, a viral antigen bound to the viral group-reactive antibody, the positive control antibody present in the positive serum bound to the viral antigen, and the labeled reagent bound to the positive control antibody. The wells in which negative control serum is applied result in microparticles having a bound viral group-reactive antibody and a viral antigen bound to the viral group-reactive antibody. The purpose of the serum controls is to ensure that the antigens in the assay are reacting with the antibodies of interest as expected (to verify quality and accuracy).

At 207, positive and negative control serum is applied to select wells 208 containing sets of microparticles having a bound viral group-reactive antibody and a negative control antigen pretreated on the microparticles. The wells in which positive control serum is applied contain microparticles having a bound viral group-reactive antibody. The positive control antibodies bind with the negative control antigen, and the labeled reagent binds with the positive control antibodies. In a washing step, the positive control antibodies bound to the negative control antigen are washed away as the negative control antigen is not commonly bound to the viral group-reactive antibody. In this way, both positive control and negative control wells 208 act as a negative control, and labeled reagent will not be detected by analyzing microparticles in this area of the plate using a flow instrument. Any combination, order, or delineation between experiments or assays within wells in the plate can be used, however the use of negative control antigens and positive and negative controls of both the viral antigen experiments or assays and the negative control antigen experiments or assays can improve overall assay quality control.

Example 5

Figure 3:
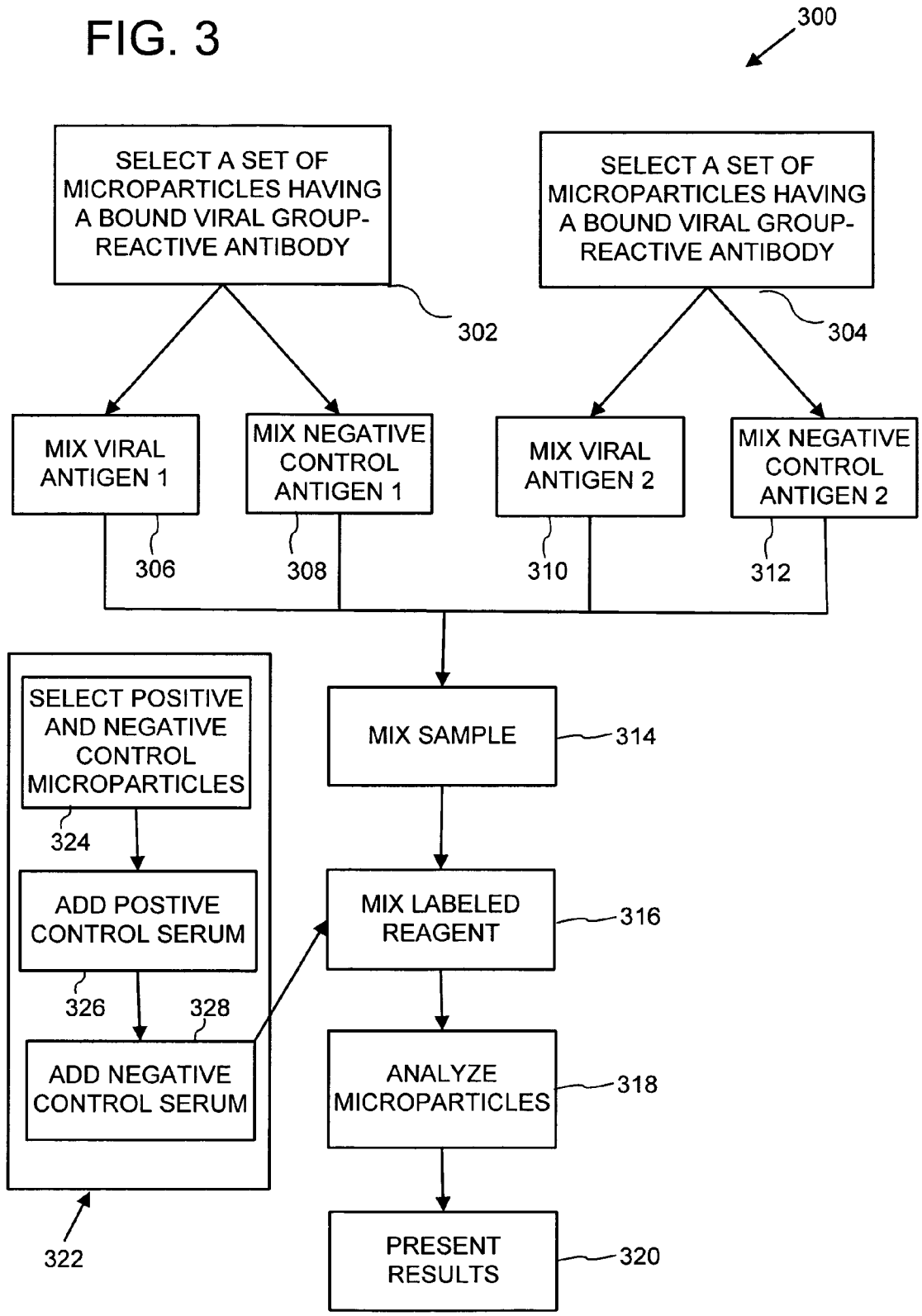
FIG. 3 is a flowchart showing another exemplary method for determining the presence or absence of antibodies of interest in a sample with a set of microparticles to which a viral group-reactive antibody is covalently bound.

Another Exemplary Method for Determining the Presence or Absence of Antibodies of Interest in a Sample FIG. 3 shows another exemplary method 300 for determining the presence or absence of antibodies of interest in a sample with a set of microparticles to which a viral group-reactive antibody is covalently bound. The method can detect the presence (or absence) of a first antibody of interest and/or a second antibody of interest in the sample and can make use of a viral group-reactive antibody for the viral group corresponding to the two antibodies of interest.

At 302, a first set of microparticles having a bound viral group-reactive antibody is selected. The first set of microparticles has at least one characteristic classification parameter which distinguishes the first set of microparticles from other sets when multiple sets of microparticles are combined in a well in a plate or the like.

At 304, a second set of microparticles having the same bound viral group-reactive antibody as the set 302 is selected. The second set of microparticles has at least one characteristic classification parameter which distinguishes the second set of microparticles from other sets when multiple sets of microparticles are combined in a well in a plate or the like.

At 306, a viral antigen type "1" corresponding to the first viral antibody of interest is mixed with a subset of the first set of microparticles having the bound viral group-reactive antibody. The viral antigen "1" reacts with the first viral antibody of interest and can become bound to the microparticles. This action of the method can be skipped (e.g., if a subset of microparticles are initially provided with viral antigen type "1" bound to the viral group-reactive antibody on a first set of microparticles).

At 308, a negative control antigen type "1" corresponding to viral antigen "1" (and therefore the first antibody of interest) is mixed with a subset of the first set of microparticles having the bound viral group-reactive antibody. The negative control antigen "1" can be bound with the first viral antibody of interest or can be loosely associated with the microparticles. This action of the method can be skipped (e.g., if a subset of microparticles bound with the viral group-reactive antibody are initially provided pretreated with negative control antigen type "1" on a first set of microparticles).

At 310, a viral antigen type "2" corresponding to the second viral antibody of interest is mixed with a subset of the second set of microparticles having the bound viral group-reactive antibody. The viral antigen type "2" reacts with the second viral antibody of interest and can become bound to the microparticles. This action of the method can be skipped (e.g., if a set of microparticles are initially provided with viral antigen type "2" bound to the viral group-reactive antibody on a second set of microparticles).

At 312, a negative control antigen type "2" corresponding to viral antigen type "2" (and therefore the second viral antibody of interest) is mixed with a subset of the second set of microparticles having the bound viral group-reactive antibody. The negative control antigen type "2" can be bound with the second viral antibody of interest or can be loosely associated with the microparticles. This action of the method can be skipped (e.g., if a subset of microparticles bound with the viral group-reactive antibody are initially provided pretreated with negative control antigen type "2" on a second set of microparticles).

At 314, sample serum is mixed with the subsets. For example, the subsets can be distributed in a multi-well plate 200 such as shown in FIG. 2, where the negative control antigen types "1" and "2" microparticles are combined in the same wells and the viral antigen types "1" and "2" microparticles are combined in the same wells. In such a way, multiplexed analysis is achievable. Washing can be done after the serum is applied to ensure that unbound compositions are not present.

At 316, labeled reagent reactive with antibodies of interest in the sample is mixed with the subsets to react with microparticles and any unbound compositions present. Washing can again be done after the labeled reagent is applied to ensure that compositions not bound to the microparticles are not present prior to analyzing the microparticles.

At 318, the subsets of microparticles are analyzed for both the presence of particular characteristic classification parameters to distinguish the microparticle sets (e.g., the first set 302 and the second set 304) and the presence or absence of antibodies of interest (e.g., as indicated by the presence of labeled reagent). For example, this can be done via a flow instrument and automated analysis system as shown in system 100 of FIG. 1A.

At 320, the results of the analysis 318 can be presented. For example, a test result can indicate the presence or absence of antibodies of interest in the sample based on the presence or absence of antibodies of interest bound to microparticles. This action can be skipped and/or the results of the analysis 318 can be stored or communicated for later use.

At 322, positive and negative controls can be run while the samples are run on the assay. For example, positive and negative controls can be run using the viral antigens (e.g., positive and negative serum controls can be mixed with viral antigens bound to viral group-reactive antibodies bound to microparticles in select wells 206 of plate section 205 as shown on plate 200 in FIG. 2) and the negative control antigens (e.g., positive and negative serum controls can be mixed with negative control antigens pretreated to microparticles in select wells 208 of plate section 207 as shown on plate 200 in FIG. 2).

At 324, positive and negative control microparticles are selected.

At 326, positive control serum is mixed with microparticles in select wells of the plate. Subsequently, labeled reagent is mixed with the microparticles as with the other microparticles at 316.

At 328, negative control serum is mixed with microparticles in select wells of the plate. Subsequently, labeled reagent is mixed with the microparticles as with the other microparticles at 316.

Controls can be useful for determining background noise in the method, as well as determining the validity of results based on known positives and negatives. Gathering background data allows for the ability to ensure accuracy by accounting for background noise in the analysis.

Example 6

Figure 4A:
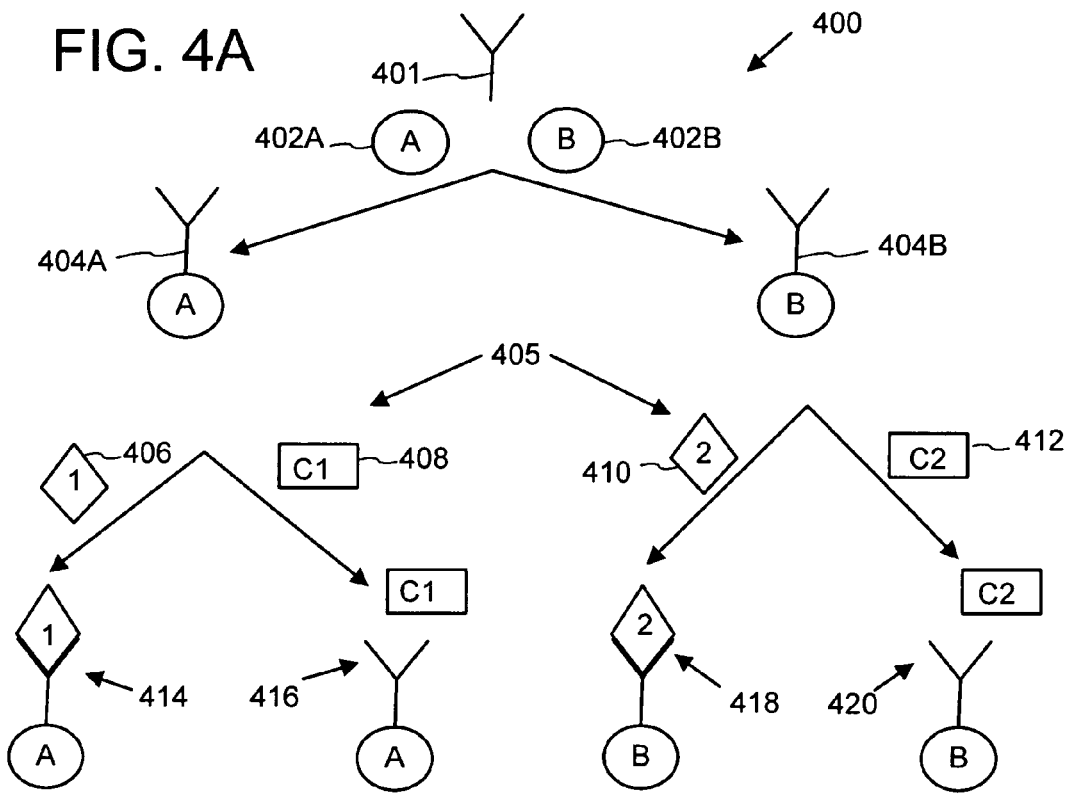
FIGS. 4A and 4B illustrate microparticles during the steps of the exemplary method shown in FIG. 3.
Figure 4B:
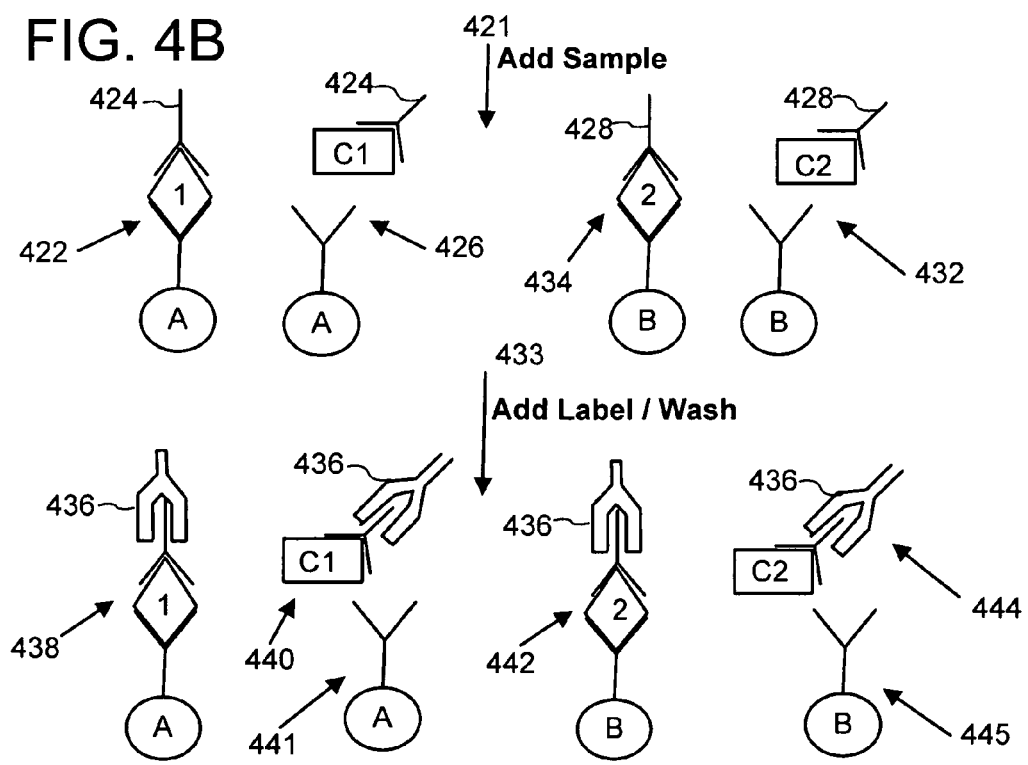

Exemplary Illustration of Microparticles During an Exemplary Method for Determining the Presence or Absence of Antibodies of Interest in a Sample FIGS. 4A and 4B illustrate exemplary microparticles during the steps of the exemplary method shown in FIG. 3.

At 400, microparticles consisting of two types of microparticles, microparticles 402A (illustrated as microparticle type "B") and microparticles 402B (illustrated as microparticle type "A") with distinguishable classification characteristic parameters and without reactive particles bound are formed or provided. Each microparticle type has the same viral group-reactive antibody 401 covalently bound to each bead type (bead type "A" or "B"), resulting in microparticles 404A (a combination of antibody 401 and microparticle 402A) and microparticles 404B (a combination of antibody 401 and microparticle 402B). Each bead within a bead type (e.g., bead type "A" or "B") has one or more distinguishable classification parameters in common with beads of the same type to allow for determination of bead types.

At 405, first and second sets of the microparticles are selected by microparticle type (as shown in 302 and 304 of FIG. 3). First set 404A is subdivided into two subsets and second set 402 is subdivided into two subsets.

One subset of the first set 404A is mixed with viral antigen type "1" 406 (as shown in 306 of FIG. 3) forming the microparticle 414, wherein the viral antigen type "1" is bound with the viral group-reactive antibody 401 bound to the microparticle.

Another subset of the first set 404A is mixed with negative control antigen type "1" 408 (as shown in 308 of FIG. 3) forming a pretreated microparticle 416. Negative control antigen type "1" does not commonly bind with the viral group-reactive antibody.

Similarly, one subset of the second set 404B is mixed with viral antigen type "2" 410 (as shown in 310 of FIG. 3) forming the microparticle 418, wherein the viral antigen type "2" is bound with the viral group-reactive antibody 401 bound to the microparticle.

Another subset of the second set 404B is mixed with negative control antigen type "2" 412 (as shown in 312 of FIG. 3) forming a pretreated microparticle 420. Negative control antigen type "2" does not commonly bind with the viral group-reactive antibody.

At 421, sample is mixed with the first and second sets of microparticles (as shown in 314 of FIG. 3). Assuming the sample has both antibodies of interest which are tested for in the assay (antibodies of interest type "1" 424 and "2" 428 of the same viral group), microparticles 422, 426, 434, and 432 are formed.

Microparticle 422 includes antibody of interest type "1" 424 bound with viral antigen type "1" 406 which in turn is bound with the viral group-reactive antibody 401 bound to the microparticle. In practice, microparticles 422 can reside in wells 202 of plate 200 as shown in FIG. 2.

Microparticle 426 includes the pretreated microparticle 416 and control antigen type "1" 408 bound with antibody of interest type "1" 424. In practice, microparticles 426 can reside in wells 204 of plate 200 as shown in FIG. 2.

Microparticle 434 includes antibody of interest type "2" 428 bound with viral antigen type "2" 410 which in turn is bound with the viral group-reactive antibody 401 bound to the microparticle. In practice, microparticles 434 can reside in wells 202 of plate 200 as shown in FIG. 2.

Microparticle 432 includes the pretreated microparticle 420 and control antigen type "2" 412 bound with antibody of interest type "2" 428. In practice, microparticles 432 can reside in wells 204 of plate 200 as shown in FIG. 2.

At 433, labeled reagent is mixed with the first and second sets of microparticles (as shown in 316 of FIG. 3) and subsequently washed. Again, assuming the sample has both antibodies of interest tested for in the method (antibodies of interest type "1" 424 and "2" 428 of the same viral group), microparticles 438, 441, 442, 445 are formed.

Microparticle 438 includes microparticle 422 bound with labeled reagent 436 (for example, a labeled antibody reactive with the antibodies of interest in the viral group). In practice, microparticles 438 can reside in wells 202 of plate 200 as shown in FIG. 2.

Microparticle 441 includes microparticle 404A with the control antigen type "1" 408 not bound with the microparticle and complex 440 where the control antigen type "1" 408 is bound with antibody of interest type "1" 424 which is bound with labeled reagent 436. In practice, microparticles 441 can reside in wells 204 of plate 200 as shown in FIG. 2 and complex 440 is washed away from the plate. Therefore, one would expect that there would be no binding of antibodies of interest type "1" to microparticles not bound with antigen type "1," serving the purpose as a negative control as it is expected that there would be no labeled reactant present. Any labeled reactant present having bound to the microparticle (indicating a bound antibody of interest type "1" bound to the microparticle) would be background noise in the assay.

Microparticle 442 includes microparticle 434 bound with labeled reagent 436 (for example, a labeled antibody reactive with the antibodies of interest in the viral group). In practice, microparticles 442 can reside in wells 202 of plate 200 as shown in FIG. 2.

Microparticle 445 includes microparticle 404B with the control antigen type "2" 412 not bound with the microparticle and complex 444 where the control antigen type "2" 412 is bound with antibody of interest type "2" 428 which is bound with labeled reagent 436. In practice, microparticles 445 can reside in wells 204 of plate 200 as shown in FIG. 2 and complex 444 is washed away from the plate. Therefore, one would expect that there would be no binding of antibodies of interest type "2" to microparticles not bound with antigen type "2," serving the purpose as a negative control as it is expected that there would be no labeled reactant present. Any labeled reactant present having bound to the microparticle (indicating a bound antibody of interest type "2" bound to the microparticle) would be background noise in the assay.

Upon analysis of the microparticles by a flow instrument, data can be generated reflecting the microparticle type ("A" or "B") and whether labeled reactant is present or not. In the example described, wherein both antibodies of interest are present in the serum sample, microparticles 438 and 442 reside in wells 202 of plate 200 as shown in FIG. 2. Therefore, the flow instrument will indicate both microparticle types as having the labeled reactant (and therefore the antibodies of interest in the sample). Similarly, the microparticles exposed to or pretreated with negative control antigens will not be read as having the labeled reactant by a flow instrument (since the negative control antigens 408 and 412 bound the antibodies of interest 424 and 428, and the complexes 440 and 444 were washed away from the microparticles prior to being read by the flow instrument).

Results can indicate the presence or absence of antibodies of interest in the sample based on the presence or absence of antibodies of interest bound to microparticles.

Additionally, positive and negative control serum controls can be a part of the assay (not shown).

Example 7

Exemplary Negative Control Antigen Pretreated Microparticles

As described in FIGS. 3 and 4, negative control antigens can be mixed with subsets of the first and second sets of microparticles having the bound viral group-reactive antibody (for example, of types "A" and "B") to form negative control antigen pretreated microparticles. Alternatively, negative control antigens can be mixed with different microparticle sets having the bound viral group-reactive antibody (for example, microparticles of types "C" and "D") to form negative control antigen pretreated microparticles. This can reduce the number of wells needed to conduct the assay (i.e., it allows for negative control antigen pretreated microparticles to be in the same wells as viral antigen microparticles while still having a manner in which to differentiate between the negative control antigen pretreated microparticles and the viral microparticles).

Example 8

Exemplary Computer-Implemented Method for Determining the Presence or Absence of Antibodies of Interest in a Sample FIG. 5 shows an exemplary computer-implemented method 500 for determining the presence or absence of antibodies of interest in a sample. The method 500 can be performed, for example, to analyze data indicating the presence or absence of microparticles such as those shown in FIG. 3. The method described in this or any of the other examples can be a computer-implemented method performed via computer-executable instructions in one or more computer-readable media. Any of the actions shown can be performed by software incorporated within a flow instrument, or a flow instrument can output data which is classified by a system external to the flow instrument.

At 502, information indicating at least one characteristic classification parameter of microparticles in an assay can be received. For example, the information can be received from a flow instrument analyzing the microparticles in an assay and indicate the presence or absence of types of microparticles (e.g., type "A" or type "B" as shown in FIG. 4.

The microparticle data can be classified based on the at least one characteristic classification parameter. For example, microparticles of type "A" as shown in 402A of FIG. 4 can be classified (e.g., distinguished) from microparticles of type "B" as shown in 402B of FIG. 4. Such classification enables the determination of the presence of microparticles labeled with different viral (and negative control) antigens. A simple mapping can be used to associate a microparticle type with an antibody on the corresponding antigen.

At 506, information indicating the presence or absence of a labeled reagent associated with classified microparticles can be received. For example, the information can be received from a flow instrument analyzing the microparticles in an assay.

At 508, the presence or absence of viral group antibodies of interest based on the presence or absence of the labeled reagent associated with the classified microparticles is determined. The determination can be done as part of the overall method 500 shown, or as a separate method in and of itself.

At 510, the results of the determination 508 can be presented. For example, the results can indicate a positive or negative result of the presence of viral antibodies of interest in a sample.

The data from any of the actions can be stored so that different actors might perform any one or more of the actions independently (e.g., for use in subsequent actions).

Example 9

Another Exemplary Computer-Implemented Method for Determining the Presence or Absence of Antibodies of Interest in a Sample FIG. 6 shows an exemplary computer-implemented method 600 for determining the presence or absence of viral group antibodies of interest based on the presence or absence of a labeled reagent associated with microparticles pre-classified by at least one characteristic classification parameter. The method 600 can be performed, for example, to analyze data from any of the examples herein that indicate the presence or absence of microparticles in an assay using a serum, CSF (cerebrospinal fluid), plasma or the like sample, such as shown in FIG. 4.

At 602, data indicating the presence or absence of a labeled reagent associated with microparticles pre-classified by at least one characteristic classification parameter is received. Such data can come from a flow instrument or the like. For example, median fluorescent intensities or indices (MFIs) for each microparticle set in each well of a plate (e.g., wells in plate 200 of FIG. 2) can be determined, with the fluorescence representative of the presence of labeled reagent (and therefore, the presence of the corresponding antibody of interest that is bound to the antigen type on the microparticle). In particular, the MFIs can represent the amount of labeled reagent on 100 beads per set. Therefore, MFIs for each microparticle set can be calculated for each well in a multi-well plate (such as shown in FIG. 2). This results in viral MFIs (of type "1" and/or type "2" antigens) in wells 202 of plate section 201 of FIG. 2, negative control antigen MFIs (background noise reactions for type "1" and/or type "2" antigens) in wells 204 of plate section 203 of FIG. 2, and positive and negative control MFIs from wells 206 and 208 of plate sections 205 and 207 of the FIG. 2.

At 604, the received data is standardized to allow for the comparison and classification of two types of antibodies of interest tested for in the microparticle assay.

At 606, data indicating microparticles are classified for the presence or absence of viral group antibodies of interest based on the standardized data.

At 608, the results of classification 606 can be presented. For example, the results can indicate the presence or absence of antibodies of interest in a sample. In the alternative, the classified microparticle data can be stored or distributed for further analysis.

Example 10

Figure 7:
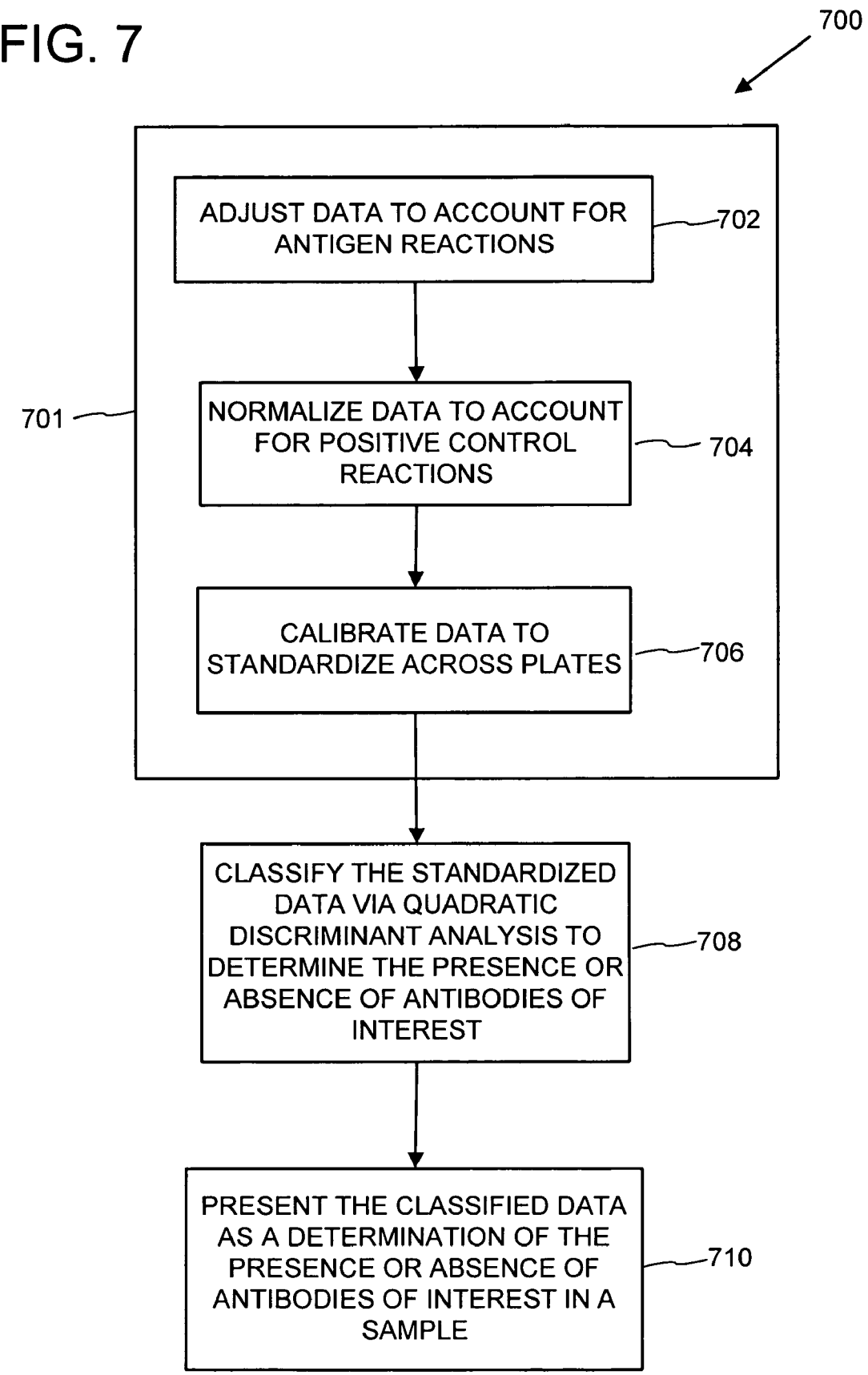
FIG. 7 is a flowchart showing an exemplary method for both standardizing data received indicating the presence or absence of a labeled reagent associated with microparticles treated with a sample and pre-classified by at least one characteristic classification parameter, and classifying the standardized data to determine the presence or absence of antibodies of interest in the sample.

Exemplary Method for Standardizing and Classifying Microparticles to Determine the Presence or Absence of Antibodies of Interest in a Sample FIG. 7 shows an exemplary method 700 for both standardizing data received indicating the presence or absence of a labeled reagent associated with microparticles treated with a sample and classified by at least one characteristic classification parameter, and classifying the standardized data to determine the presence or absence of antibodies of interest in the sample.

At 701, an exemplary method is shown for standardizing data received indicating the presence or absence of a labeled reagent associated with microparticles treated with a sample and pre-classified by at least one characteristic classification parameter (e.g., action 604 of FIG. 6) For example, data received from the flow instrument analysis of the microparticles in the wells of an assay plate 200 can be standardized.

At 702, the data (e.g., MFI data 602 of FIG. 6) can be adjusted to account for antigen reactions. Data representing the presence of labeled reagent by the flow instrument can be represented as MFI, or the median of the fluorescent label detected in the plurality of microparticles of the same type. For example, data representing the presence of labeled reagent in microparticles having a viral antigen bound to both a viral group-reactive antibody and a viral antibody of interest (for example, data representing microparticles such as microparticle 438 of FIG. 4 or data representing positive control microparticles) can be divided by data representing the presence of labeled reagent in microparticles pretreated with negative control antigen (for example, data representing a situation in which complex 440 is bound to microparticle 441 in some fashion) to determine adjusted data. Equations (1) and (2) illustrate the adjusting of data:

$$MFI_{viral\ antigen\ 1}/MFI_{negative\ control\ antigen\ 1} = Adj\ MFI_{antigen\ 1} \quad (1)$$

$$MFI_{viral\ antigen\ 2}/MFI_{negative\ control\ antigen\ 2} = Adj\ MFI_{antigen\ 2} \quad (2)$$

In such a manner "background noise" is detected and accounted for in the assay.

At 704, the data can be normalized to account for the positive control reactions. For example, data representing the presence of labeled reagent in microparticles having a first viral antigen bound to the viral group-reactive antibody and a positive control antibody (for example, data representing microparticles to which a select positive control serum has been applied such as at 326 of method 300 of FIG. 3, and in a well 206 of plate 200) can be divided by data representing the presence of labeled reagent in microparticles having a second viral antigen bound to the viral group-reactive antibody and a second positive control antibody (for example, data representing microparticles to which a second select positive control serum has been applied, such as at 326 of method 300 of FIG. 3, and in another well within plate section 205 of plate 200) to determine a normalizing factor. Equation (3) illustrates the normalizing of data:

$$Adj\,MFI_{positive\,control\,viral\,antigen\,1}/ \\ Adj\,MFI_{positive\,control\,viral\,antigen\,2} = \\ \text{Normalizing factor} \qquad (3)$$

In such a manner, the reaction rate differences between different viral antigens and their corresponding antibodies of interest can be accounted for to allow for direct comparisons between differing viral antibodies of interest within the same viral group. The normalizing factor can then be multiplied by the adjusted data from 702.

At 706, the data can be calibrated to allow for standardization across multiple plates. For example, positive and negative control data for each antigen in the assay can be compared to corresponding averaged data of multiple plates via inverse linear regression to determine relationships. In this way, data from different labs can be compared to one another given that the same controls are used.

At 708, the standardized data can be classified via quadratic discriminant analysis to determine the presence or absence of antibodies of interest. For example, logarithmic transformation (e.g., $\log_{10}$ or any other logarithmic transformation) of the calibrated data can be done to normalize the data allowing for comparisons between groups of microparticle data. Other methods of normalizing the data can also be used. Quadratic discriminant analysis (QDA) (which assumes normality) can then be used on the normalized data to determine a discrimination line for determining whether the data from a microparticle or groups of microparticles represents the presence or absence of a viral group antibody of interest in a sample (i.e., classifying the data).

At 710, the classified data can be presented as a determination of the presence or absence of antibodies of interest in a sample. For example, logarithmic transformations of the data (such as is done at 708) can be presented on a plot where the logarithmic transformations for each antigen are plotted against one another with the discrimination line (as determined at 708) as a visual representation of the presence or absence of viral group antibodies of interest in the sample. Additionally, logarithmic transformations of the data can be presented as a classification probability surface where three dimensional plots of the data represent the classification probabilities computed on a grid over the range of data. In such a classification probability surface, the bottom of the trough on the classification surface is the discrimination line determined at 708. Other ways of presenting the data can be simple yes/no designations of antibodies of interest being present in the sample, tabular presentation of the data, and the like. The presentation of data can be skipped or incorporated into another method for further analysis or display.

Example 11

Exemplary Results Indicating the Presence or Absence of Antibodies of Interest in a Sample In any of the examples herein, exemplary results of the described methods can result in quantitative data representing the presence or absence of antibodies of interest in a sample. If cross-reactive antibodies of interest are present in the sample, the more prevalent antibody of interest can be identified. If desired, simple indicators (e.g., "yes" or "no"; "positive" or "negative"; "green" or "red") can be used.

Similarly, standardized results data from the described methods can be potentially useful. Additionally, results indicating the presence or absence of antibodies of interest in a sample can be represented as probabilities or likelihoods of presence or absence. Such probabilities can be indicated in output results, used to choose the most likely classification result (e.g., which is indicated in output), or both.

Example 12

Exemplary Method for Increasing Specificity of Methods for Determining the Presence or Absence of Antibodies of Interest in a Sample In any of the examples herein, nonspecific reactors can be determined to further classify the results of the determination of the presence or absence of antibodies of interest in a sample. Cut off ratios can be defined and in such a manner that specificity of sample antibody-antigen reactions can be determined (e.g., specific, antigen "1" nonspecific, antigen "2" nonspecific, and nonspecific to both antigen "1" and antigen "2"). Any nonspecific classifications can replace initial classifications to give more informative classification results.

Example 13

Exemplary Method for Confirming the Determination of the Presence or Absence of Antibodies of Interest in a Sample In any of the examples herein, a confirmation of the determination of the presence or absence of antibodies of interest in a sample can be determined by PRNT assay or the like. Cut off determinations can be used to determine whether or not this confirmation is needed, thereby decreasing the need to regularly order confirmatory PRNT assays. For example, maximum absolute differences between classification probabilities, specificity results, and extrapolation determinations can be used to determine the need for a confirmation assay. Whether a confirmatory assay is determined as needed can be indicated in output results.

Example 14

Exemplary Operation of Method for Standardizing and Classifying Microparticles to Determine the Presence or Absence of Antibodies of Interest in a Sample using Arbovirus Data For purposes of describing exemplary operation of method 700 of FIG. 7, an exemplary execution of the method using experimental arbovirus microparticle data follows.

An example of exemplary MFI data received from a flow instrument (for example, received data 602 of FIG. 6) is shown in Table A.

TABLE A

| Sample ID | SLE-VAg | WN-VAg | SLE-NegAg | WN-NegAg |
| --- | --- | --- | --- | --- |
| 1 | 27 | 949 | 15 | 10 |
| 2 | 172 | 48 | 118 | 11 |
| 3 | 1391 | 199 | 18 | 13 |
| 4 | 222 | 7810 | 17 | 12 |
| 5 | 17 | 5 | 12 | 13 |
| 6 | 771 | 255 | 13 | 9 |
| 7 | 22 | 14 | 52 | 56 |

TABLE A-continued

| Sample ID | SLE-VAg | WN-VAg | SLE-NegAg | WN-NegAg |
|---|---|---|---|---|
| 8 | 20 | 392 | 11 | 5 |
| WN + Control | 47 | 2750 | 25 | 21 |
| SLE + Control | 1198 | 360 | 16 | 10 |
| Neg Control | 22 | 13 | 14 | 10 |

The average MFI of duplicate wells are represented in Table A. SLE-VAg represents Saint Louis encephalitis viral antigen microparticles (antigen 2), WN-VAg represents West Nile viral antigen microparticles (antigen 1), SLE-NegAg represents Saint Louis encephalitis negative control antigen microparticles (negative control antigen 2), WN-NegAg represents West Nile negative control antigen microparticles (negative control antigen 1).

The MFI data received (as shown in Table A) can be adjusted to account for antigen reactions (e.g., to accomplish action 702 of FIG. 7). The adjusted MFIs shown in Table B are determined from the exemplary MFI data shown in Table A.

TABLE B

| Sample ID | SLE Adj | WN Adj |
|---|---|---|
| 1 | 1.8000 | 94.9000 |
| 2 | 1.4576 | 4.3636 |
| 3 | 77.2778 | 15.3077 |
| 4 | 13.0588 | 650.8333 |
| 5 | 1.4167 | 0.3846 |
| 6 | 59.3077 | 28.3333 |
| 7 | 0.4231 | 0.2500 |
| 8 | 1.8182 | 78.4000 |
| WN + Control | 1.8800 | 134.1463 |
| SLE + Control | 77.2903 | 37.8947 |
| Neg Control | 1.6000 | 1.3250 |

SLE Adj represents the adjusted MFI for Saint Louis encephalitis (antigen 2) as calculated using equation 2. For example, for sample 1, SLE Adj was determined by SLE VAg (27)/SLE NegAg (15)=1.8. WN Adj represents the adjusted MFI for West Nile (antigen 1) as calculated using equation 1. For example, for sample 1, WN Adj was determined by WN Vag (949)/WN NegAg(10)=94.9.

The adjusted MFI data (as shown in Table B) can be normalized (e.g., to accomplish action 704 of FIG. 7) to account for reaction rate differences via the normalizing factor. Table C shows SLE normalized values for the samples shown in Tables B (i.e., allowing the ability to compare SLE adjusted values with WN adjusted values by accounting for reaction rate differences via the normalizing factor). For example, SLE normalized value 3.1241 was determined for sample 1 by calculating the normalizing factor using equation 3 and multiplying it by the SLE Adj value. This can be represented as SLE Adj for sample 1*((WN Adj for WN+control)/(SLE Adj for SLE+control)), (i.e., 1.8*(134.1463/77.2903)= 3.1241).

TABLE C

| Sample ID | SLE normalized (reaction rate adjusted) values |
|---|---|
| 1 | 3.1241 |
| 2 | 2.5299 |
| 3 | 134.1246 |
| 4 | 22.6651 |
| 5 | 2.4588 |
| 6 | 102.9354 |
| 7 | 0.7343 |
| 8 | 3.1557 |
| WN + Control | 3.2630 |
| SLE + Control | 134.1463 |
| Neg Control | 2.7770 |

The adjusted and normalized MFI data can be calibrated to allow for standardization across multiple plates (e.g., to accomplish action 706 of FIG. 7) allowing for the ability to compare results to a historical standard and results from multiple labs to one another, assuming the same controls are used. The WN Adj (see Table B) and SLE normalized values (see Table C) can be standardized to historical values defined by a regression line of the controls on the plates used in assay development (allowing for the ability to compare results to a historical standard). This is achieved by dividing the adjusted values (WN Adj and SLE normalized values) by the slope of the regression line (i.e., inverse linear regression calibration to historical controls).

The standardized MFI data (i.e., the data after it has been adjusted, normalized and calibrated) can then be classified (e.g., to accomplish action 708 of FIG. 7) to determine the presence or absence of antibodies of interest. Table D shows $\log_{10}$ transformations of the calibrated data. The logarithmic transformations are done to normalize the data to allow for quadratic discriminant analysis, which assumes normality.

TABLE D

| Sample ID | WN Std $\log_{10}$ | SLE Std $\log_{10}$ |
|---|---|---|
| 1 | 1.3550 | −0.1274 |
| 2 | 0.0176 | −0.2190 |
| 3 | 0.5626 | 1.5054 |
| 4 | 2.1912 | 0.7333 |
| 5 | −1.0372 | −0.2314 |
| 6 | 0.8300 | 1.3905 |
| 7 | −1.2243 | −0.7562 |
| 8 | 1.2720 | −0.1230 |

Classifying by setting up variables and assigning values can then be done using the logarithmic normalized data. Mean vectors ($\mu_{W,i}, \mu_{S,i}$) of each group i (WN positive, SLE positive, Negative (Neg)) can be defined. Covariances (correlations) of the groups i (WN, SLE, Neg) can be defined. The mean, variance, and correlation can be defined for each normally distributed multivariate group (with two variables, $\log_{10}(W)$ and $\log_{10}(S)$, for each group, hence multivariate). Then, for each sample's $\log_{10}(W)$, $\log_{10}(S)$ pair, classification probabilities for the sample being WN positive, SLE positive, or Negative are determined. Table E shows these probabilities for the data/samples in Table D and gives a raw classification result based on the three probabilities for each sample.

TABLE E

| Sample ID | Neg Prob | WN Prob | SLE Prob | MIA Raw Result |
|---|---|---|---|---|
| 1 | 0.0000 | 1.0000 | 0.0000 | WN |
| 2 | 0.9918 | 0.0001 | 0.0081 | Neg |
| 3 | 0.0000 | 0.0000 | 1.0000 | SLE |
| 4 | 0.0000 | 1.0000 | 0.0000 | WN |
| 5 | 0.9973 | 0.0000 | 0.0027 | Neg |
| 6 | 0.0000 | 0.0000 | 1.0000 | SLE |
| 7 | 0.9944 | 0.0000 | 0.0056 | Neg |
| 8 | 0.0000 | 1.0000 | 0.0000 | WN |

In addition to a raw classification, to increase specificity of the assay, a determination of nonspecific reactors can be determined to further classify the results. Cut off ratios can be defined. A nonspecific reactor can be defined by one or more exemplary characteristics. For example, a nonspecific reactor can be defined as having both of the following exemplary characteristics: 1) A raw MFI when reacted on the viral antigen of >a multiple representing the mulitiplicity of the lowest MFI value seen for true positive WN samples (e.g., 8)×the negative control MFI (for WN antigen) or >a multiple representing the multiplicity of the lowest MFI value seen for true positive SLE samples (e.g., 5)×the negative control MFI (for SLE antigen); and 2) a $\log_{10}(W)$ value of <the lowest $\log_{10}(W)$ value (WN antigen) seen for true positive WN samples (e.g., 0.857) or a $\log_{10}(S)$ value of <the lowest $\log_{10}(S)$ value (SLE antigen) seen for true positive SLE samples (e.g., 0.549). In such a manner specificity can be named four different ways: Specific, SLE Nonspecific, WN Nonspecific, and Nonspecific for both antigens. Any Nonspecific classifications can replace the raw classification result to give a specific MIA classification result. However, exceptions for using any nonspecific classification to replace the raw classification can be determined. For example, if the result is nonspecific to one antigen, but has a very convincingly positive value (e.g., a $\log_{10}$ value >=2) to the other antigen, then the MIA classification result can be given as the specific viral antigen.

Furthermore, analysis can determine whether PRNT confirmation assays are to be ordered to further confirm results. For example, if the maximum absolute difference between classification probabilities is less than a threshold (e.g., 0.7, 0.8, or the like), or the MIA result is Nonspecific, WN Nonspecific, or SLE Nonspecific then a PRNT can be recommended. Furthermore, for example, if $\log_{10}$ transformations for the calibrated data (See Table D) are both less than zero, and the data point falls outside of the negative area of the QDA when the QDA lines are extrapolated into negative values (i.e., the data point falls outside the range of the data used to derive the classification rule), then the MIA classification for such a data point will be negative (and result in an Extrapolation entry in Table F of YES).

TABLE F

| Sample ID | Specificity | MIA Specific Result | Order PRNT | Extrapolation |
|---|---|---|---|---|
| 1 | Specific | WN | No | No |
| 2 | SLENonspecific | Nonspecific | Yes | No |
| 3 | WNNonspecific | SLE | No | No |
| 4 | Specific | WN | No | No |
| 5 | Specific | Neg | No | No |
| 6 | WNNonspecific | Nonspecific | Yes | No |
| 7 | Specific | Neg | No | No |
| 8 | Specific | WN | No | No |

Table E. (MIA Raw Result) and Table F. (MIA Specific Result) is one way of presenting the classified data as a determination of the presence or absence of antibodies of interest in a sample (e.g., to accomplish action 704 of FIG. 7).

Example 15

Exemplary Experimental Results using Arboviruses

Multiplexed microparticle analysis for determining a serodiagnosis of arboviral infection was conducted utilizing an antibody (e.g., viral group-reactive antibody 401 in FIG. 4), that when coupled to bead sets (microparticles) (e.g., microparticles 402 and 404 in FIG. 4), can be used to assay for human IgM antibodies directed against any flavivirus, in this case West Nile (WN) and Saint Louis encephalitis (SLE) viruses. The use of a data standardization (and transformation) methodology (e.g., method 600 of FIG. 6) constitutes a significant departure from those used in other serological methods for arbovirology.

Since its introduction into the United States in 1999, West Nile virus has spread throughout most of the country. Human disease cases have been reported in all states except Alaska, Hawaii, and Washington, as of October 2004. A total of 9,175 human disease cases were reported to CDC ArboNET for 2003. The related flavivirus Saint Louis encephalitis virus is endemic in the U.S. A total of 4,482 confirmed human disease cases of SLE have been documented between 1964 and 2000. The last major outbreak of SLE in the U.S. occurred in 1974-1977, when more than 2,500 human SLE disease cases were reported. WN and SLE virus infections often present with similar clinical profiles. Symptoms common to both diseases may include sudden onset of fever, headache, and myalgia in mild cases; and disorientation, meningitis, and encephalitis in severely affected patients. WN virus can produce a rash, and flaccid paralysis has been reported in some cases. Both WN and SLE viruses belong to the Japanese encephalitis virus serocomplex of viruses. Not only do they share many clinical manifestations but they are serologically similar.

A total of 990 frozen human serum specimens were used in this study. These were obtained from the specimen archive at CDC's Division of Vector-Borne Infectious Diseases, Arboviral Diseases Branch, Diagnostics and Reference Laboratory (CDC/DVBID/ADB); and as gifts from CDC/DVBID/Bacterial Zoonoses Branch (B ZB); CDC/DVBID/Dengue Branch (DB); Arizona Department of Health Services (AZDHS) and Focus Technologies (Cypress, Calif.). The sets and subsets of sera, and the numbers of samples are detailed in FIG. 8.

Anti-WN IgM-positive, anti-SLE IgM-positive control human sera, and pooled antibody-negative sera, were obtained from the DVBID/ADB/DRL. These specimens were used throughout 2003 in the diagnostic MAC-ELISAs.

All serum and CSF samples (except for the syphilis, antinuclear antibody (ANA), rheumatoid factor (RF), and Lyme Disease serum panels) were tested for IgM antibodies to WN and SLE viruses by using the MAC-ELISA technique described in Martin et al. 2000. "*Standardization of immuno-* globulin M capture enzyme-linked immunosorbent assays for routine diagnosis of arboviral infections. J. Clin. Microbiol. 20:754-790, which is hereby incorporated by reference. Sera were diluted 1:400 in wash buffer; CSF specimens were used undiluted. The WN viral antigen used was a WN virus envelope-premembrane (E-prM) recombinant protein secreted in transformed COS-1 cells at the CDC; the inactivated SLE viral antigen was produced in suckling mouse brain as described in Clarke, D. H., and J. Casals. 1958. *"Techniques for hemagglutination and hemagglutination-inhibition with arthropod-borne viruses. "Am. J. Trop. Med. Hyg.* 7:561-573, which is hereby incorporated by reference. Control antigens were produced under the same conditions as the viral antigens.

Neutralizing antibody titers for 316 sera from ADB were available from the ADB diagnostic database. The PRNT method was used as described in Lindsay H S, et al. 1976. *"Serum dilution neutralization test for California group virus identification and serology. J. Clin. Microbiol.* 4:503-510, which is hereby incorporated by reference.

Carboxylated microspheres (Lot B) were purchased from Luminex Corporation (Austin, Tex.). Purified flavivirus group-reactive SLE monoclonal antibody (MAb) 6B6C-1 (14) was obtained as a gift from Hennessy Research Associates, LLC (Shawnee, Kans.). This MAb was covalently coupled to nominal beadset numbers 32 and 57 using the Lot B method provided by Luminex Corporation. Briefly, 5 million each of bead sets 32 and 57 were activated using 10 µl of 50 mg/ml sulfo-NHS (Pierce Chemical Co., Rockford, Ill.) and 10 µl of 50 mg/ml 1-ethyl-3-(3-dimethylamino-propyl) carbodiimide-HCl at pH 6.3 in the dark for 20 minutes on a rotary mixer. Twenty-five micrograms of 6B6C-1 were coupled to each bead set at pH 6.0 with 2 h incubation in the dark on the rotary mixer. Unused sites on the coupled microspheres were blocked with 1% BSA in PBN (PBS with 0.05% BSA and 0.02% sodium azide) for 30 min. Bead concentrations were adjusted to $2 \times 10^6$ beads/ml and stored in PBN at 4° C. To determine qualitatively if coupling of the antibody to the beads was successful, 100 beads/µl in MIA buffer (PBS with 1% BSA (Sigma Chemical Company, St. Louis, Mo.)) were reacted with 4 µg/ml R-phycoerythrin (R-PE)-conjugated anti-mouse IgG (PE) (Jackson Immunoresearch, West Grove, Pa.). Reactions were read on a BIO-PLEX instrument (Bio-Rad Laboratories, Inc., Hercules, Calif.).

Antigens were added to the coupled bead sets prior to performing the duplex MIA. Recombinant WN virus E-prM protein expressed in COS-1 cells and negative COS-1 antigen control purified by ultracentrifugation, was obtained as a gift from Focus Technologies and SLE suckling mouse brain and negative antigens were obtained from the DVBID/ADB reference collection. Two and a half million 6B6C-1-coupled bead set 32 were added to 125 µg of WN viral antigen in a 5-ml volume of MIA buffer (e.g., action 306 of method 300 in FIG. 3). Negative recombinant antigen was added to 2.5 million beads of the same set (e.g., action 308 of method 300 in FIG. 3). These were incubated with rotation in the dark at room temperature for 1 hr, and then stored for up to a month at 4° C. The same procedure was used to add the SLE viral (e.g., action 310 of method 300 in FIG. 3) and negative suckling mouse brain antigens (e.g., action 312 of method 300 in FIG. 3) to 6B6C-1-coupled bead set 57. The viral protein concentration of the SLE virus antigen was unknown; however, the optimal volume of antigen per the 5-ml preparation was 25 µl, as determined by titration. The same amount was used for the negative control antigen.

Positive and negative serum controls were processed to remove IgG antibodies using Mini Rapi-sep units (PanBio, Baltimore, Md.) according to the manufacturer's instructions, resulting in a 1:8 dilution of the serum. The processed control serum can be stored for up to a month at 4° C. The relative amounts of IgM in the WN and SLE positive controls were determined via an MIA test using microspheres coupled to goat anti-human IgM (Kirkegaard and Perry Laboratories, Gaithersburg, Md.) and detected using an anti-human IgM R-PE conjugate (Jackson Immunoresearch, West Grove, Pa.) using a BIO-PLEX instrument. The MFIs indicated that the IgM concentrations of the anti-WN and anti-SLE IgM-positive control sera were equivalent, and, therefore, no adjustment to the concentrations of the controls was necessary. Prior to use in the duplex MIA the control serum samples were adjusted to a final dilution of 1:400 using MIA buffer.

The following method was used to deplete IgG from the test serum specimens: A 96-well filter plate (Millipore Corporation, Billerica, Md.) was pre-wetted with PBS, and a slurry containing 5 µl per well of protein G sepharose 4 fast flow (Amersham Biosciences, Uppsala, Sweden) was added. The sepharose matrix was washed twice with PBS using a vacuum manifold (Millipore Corp., Burlington, Mass.) and 100 µl of a 1:20 dilution of patient serum in PBS was added. The matrix was resuspended into the serum and the mixture was shaken on a platform for 30 min. at room temperature. The IgG-depleted serum was collected by filtration into a 96-well plate that was placed inside the vacuum manifold. The serum samples were adjusted to a final dilution of 1:400 (the optimum dilution as determined via titration) with MIA buffer before use. The success of IgG depletion using protein G was shown using WN and SLE IgG-ELISAs (6) for a few samples.

A 96-well filter plate (e.g., plate 200 of FIG. 2) was pre-wetted for 5 min. with MIA buffer, and suctioned off using a vacuum manifold. The plate was bisected vertically. Onto the left side of the plate, 50 µl of bead set 32 (2500 beads) coupled with MAb 6B6C-1 pre-treated with WN virus antigen, plus 50 µl of bead set 57 (2500 beads) coupled with MAb 6B6C-1 pre-treated with SLE antigen was added to each well (e.g., plate section 201 of FIG. 2). To the right side of the plate 50 µl of bead set 32 (2500 beads) coupled to MAb 6B6C-1 pre-treated with negative recombinant antigen, plus 50 µl of bead set 57 (2500 beads) pre-treated with negative suckling mouse brain antigen was added to each well (e.g., plate section 203 of FIG. 2). The beads were immediately washed with MIA buffer two times using the vacuum manifold. Fifty microliters of 40 prepared serum specimens were added to each side of the plate, so that all specimens were reacted on viral and negative antigens (e.g., action 314 of method 300). Prepared positive control sera were added in duplicate to each side of the plate (e.g., action 326 of method 300), and four repetitions of the negative control serum were added (e.g., action 328 of method 300) to each side of the plate (e.g., plate sections 205 and 207 of FIG. 2). Fifty microliters of 4 µg/ml anti-human IgM, Fc R-PE (Jackson Immunoresearch) diluted in MIA buffer were added to each well on the plate. The microspheres were resuspended by pipetting and the plate was incubated in the dark (to prevent the microspheres from bleaching) for 90 minutes with continual agitation on a plate shaker. The wells were washed twice with MIA buffer and the microspheres were resuspended in 100 µl of MIA buffer. The fluorescent reactions were measured and analyzed by using a BIO-PLEX instrument which simultaneously identified the individual bead sets and the reactions associated with them. All 990 serum specimens were processed in this manner.

The MFIs for each bead set in each well were generated by the BIO-PLEX instrument. The MFIs represented the amount of anti-human IgM R-PE on 100 beads per set. The raw MFI results were transformed (e.g., action 701 of FIG. 7) so that the WN and SLE results can be directly compared to one another, and so that the results were comparable plate to plate. Briefly, for each control and sample, viral antigen reaction MFIs were divided by negative antigen MFIs to give adjusted values (e.g., action 702 of FIG. 7). Mean adjusted positive control values for each plate are divided into one another to give a normalizing factor, by which all SLE adjusted values were multiplied (normalized) (e.g., action 704 of FIG. 7). The positive and negative control values for each antigen on each plate were compared using linear regression to the corresponding averaged values of the remaining plates (e.g., action 706 of FIG. 7). Using these relationships, standardized values for samples reacted on each antigen were derived by inverse linear regression. The $\log_{10}$ transforms of the standardized WN and SLE viral antigen values were calculated, and denoted as $\log_{10}(W)$ and $\log_{10}(S)$ respectively.

Figure 8:
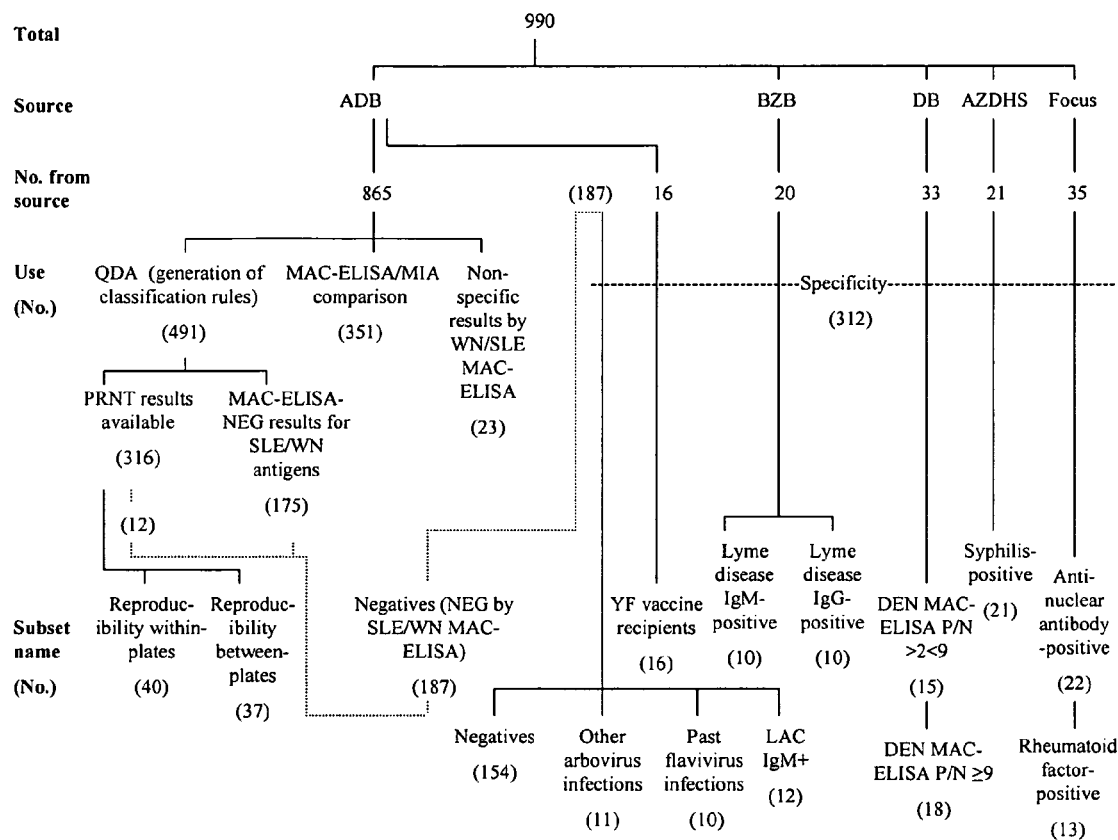
FIG. 8 illustrates the specimens used in the West Nile/Saint Louis encephalitis duplex MIA exemplary experimental study.

The $\log_{10}$ (W) and $\log_{10}$ (S) were plotted against one another for the 491 serum specimens that were used in the generation of classification rules as indicated in FIG. 8. The resulting data points were teamed with their corresponding confirmatory classifications. These data were subjected to quadratic discriminant analysis QDA (13) using S-Plus Professional, version 6.2 (Insightful Corporation, Seattle, Wash.) to determine classification rules that identified negative, anti-SLE IgM-positive, and anti-WN IgM-positive samples by the duplex MIA method (e.g., action 708 of FIG. 7). The specimens with PRNT results were collected at least 9 days post-onset of symptoms, or were PRNT-positive if the collection date was less than 9 days post-onset of symptoms. This was done to ensure that no IgM-positive, PRNT-negative results were incorporated into the analyses. Estimates of the predictive accuracy of the method were computed, and within- and between-plate repeatabilities were assessed by estimating the intraclass correlation coefficient (ICC) and associated 95% confidence intervals (CI).

Serum samples not included in the classification rule determination were evaluated by the duplex MIA, and the QDA rules applied to the data. For this analysis, 351 serum specimens were tested by the duplex MIA and the results were compared to the MAC-ELISA.

A total of 81 CSF specimens obtained from the ADB archive were chosen without regard to diagnosis. These were diluted 1:5 in MIA buffer and subjected to the same duplex MIA procedure described above for serum specimens. No pre-treatment of CSF samples with protein G was performed because of the low levels of IgG that are present in CSF. Previously tested, pooled negative human CSF served as a negative control.

Figure 9:
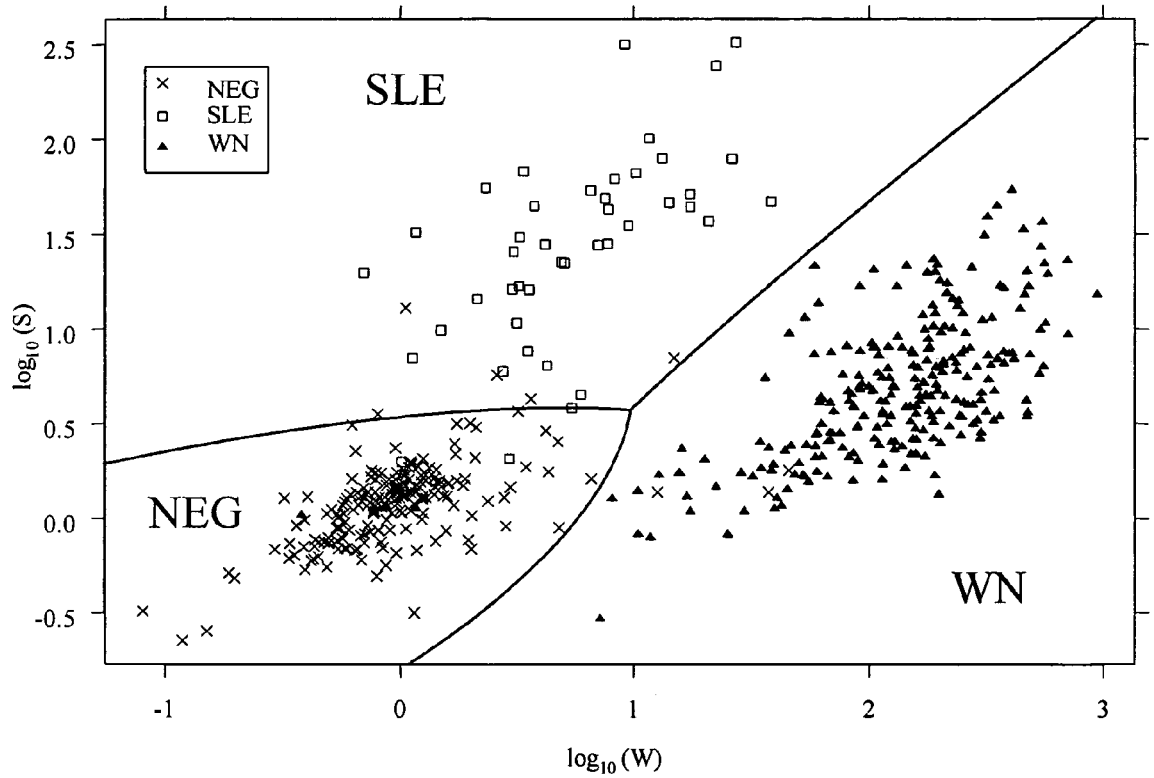
FIG. 9 illustrates an exemplary presentation of results of the exemplary determination of the presence or absence of viral group antibodies of interest in a sample.

The unprocessed MFI values for serum specimens reacting with the viral antigens in the duplex MIA reached a maximum of about 10,000 for anti-WN IgM antibodies and 6,000 for anti-SLE IgM antibodies. The positive controls typically gave MFI values of around 2,000 on the viral antigens and less than 100 on the negative antigens; the negative serum controls gave MFIs less than 100 on both viral and negative antigens. The test therefore exhibited a significant dynamic range. QDA classification regions determined using 491 specimens are shown in FIG. 9, where each specimen's true classification, based on the PRNT or negative MAC-ELISA result, is indicated.

Cross-validation results for the QDA are shown in Tables 1A and 1B below. In the tables, QDA cross-validation results and MAC-ELISA classifications are compared to the true classifications of 491 samples that were used to generate the QDA classification rules. True classification was generated by PRNT for 316 samples and by MAC-ELISA for 175 negative samples. Percent correct classification of negative samples by MAC-ELISA was 94.3% when equivocal results were not included.

TABLE 1A

Comparison to true classifications (QDA)

| True Classification | | QDA Classification | | | % Correct |
|---|---|---|---|---|---|
| Result | # Samples | Neg | SLE | WN | QDA classficiation |
| Neg | 200 | 192 | 5 | 3 | 96.0 |
| SLE | 43 | 3 | 40 | 0 | 93.0 |
| WN | 248 | 4 | 0 | 244 | 98.4 |

TABLE 1B

Comparison to true classifications (MAC-ELISA)

| True Classification | | MAC-ELISA classification | | | % Correct MAC-ELISA |
|---|---|---|---|---|---|
| Result | # Samples | Neg | SLE | WN | classification |
| Neg | 200 | 182 | 11 | 7 | 91.0 |
| SLE | 43 | 0 | 32 | 11 | 74.4 |
| WN | 248 | 5 | 2 | 241 | 97.2 |

Figure 10:
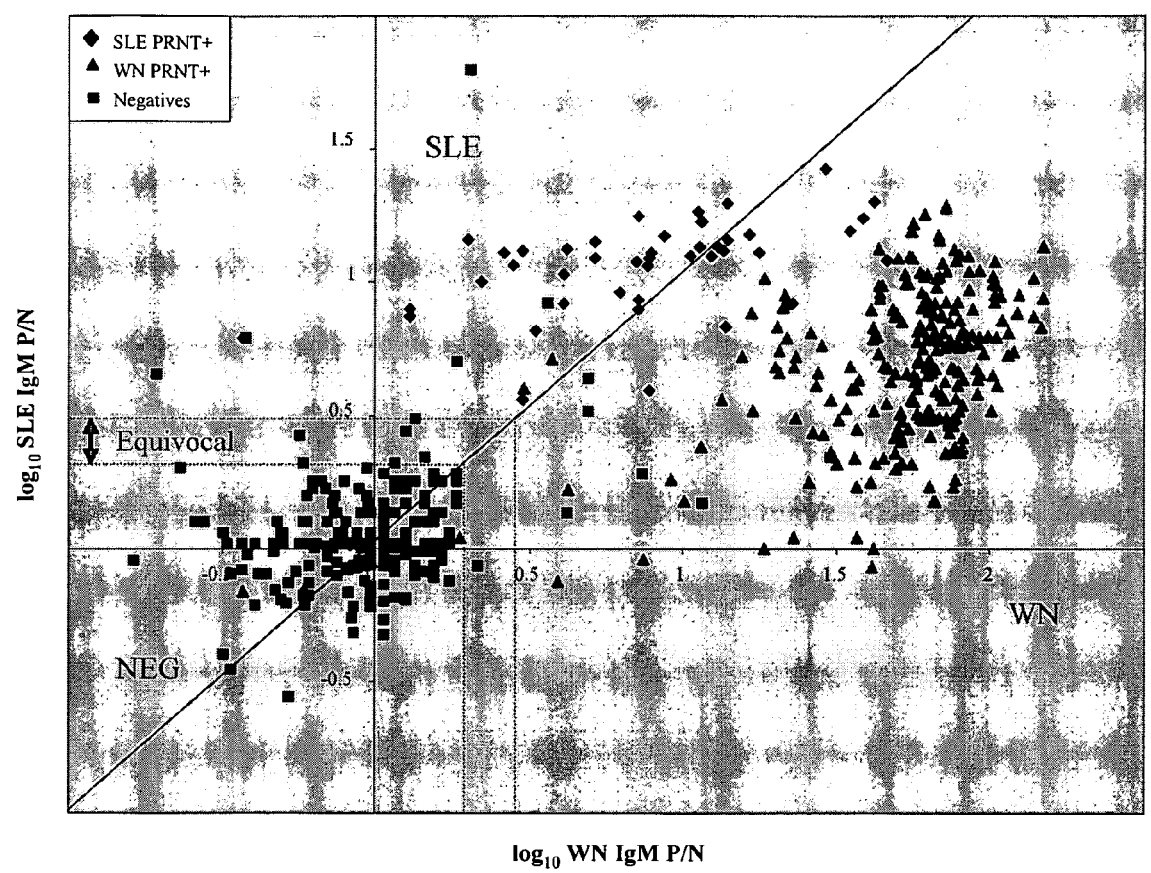
FIG. 10 illustrates the MAC-ELISA/PRNT results of an exemplary experimental study testing serum for West Nile/Saint Louis encephalitis viral infection compared to the results of the same serum tested using the exemplary techniques described herein.

The number of anti-WN IgM-positive and negative specimens available for the study was far greater than the number of available anti-SLE IgM-positive samples. In summary, cross-validation estimates of the correct classification rates for the groups were: Negative 96.0% (192/200); WN 98.4% (244/248); SLE 93.0% (40/43). The MAC-ELISA data for these same specimens were compared to their respective true classifications by plotting the $\log_{10}$ anti-WN MAC-ELISA positive-to-negative (P/N) ratios against the $\log_{10}$ anti-SLE MAC-ELISA P/N ratios as shown in FIG. 10). A line was used to separate those results that were greater for anti-WN IgM than for anti-SLE IgM. The standard algorithm for the MAC-ELISA for a sample taken day 9 after onset or later classifies results with a P/N ratio of less than 2 as negative for IgM to that antigen, and a P/N of >3 as positive for IgM. A P/N falling in between 2 and 3 is termed equivocal. Lines delineating the equivocal zone are shown in the graph. The MAC-ELISA results compared to the true classifications as follows: Negative 91% (with a P/N of <2) with 7 additional negative samples being classified as equivocal; WN 97.2%; SLE 74.4%. Table 1 shows the breakdown of these results. In addition, the QDA classifications of these samples were compared to MAC-ELISA results (see Table 2 below).

TABLE 2

QDA classifications versus MAC-ELISA classifications for the samples used in the generation of the classification rules.

| MAC-ELISA classification | QDA classification | | | |
|---|---|---|---|---|
| | Neg | SLE | WN | Total |
| Neg | 184 | 1 | 2 | 187 |
| SLE | 4 | 33 | 2 | 39 |
| WN | 4 | 11 | 243 | 258 |
| Equivocal | 7 | 0 | 0 | 7 |
| Total | 199 | 45 | 247 | 491 |

Of the eight samples that were incorrectly classified by the QDA as IgM-positive to either SLE or WN viral antigens (see Table 1), four were in agreement with the MAC-ELISA results; i.e., results from the duplex MIA and MAC-ELISA methods disagreed with the PRNT values. None of these four specimens were collected less than nine days after onset of symptoms, suggesting that a small percentage of patients were either unusually late in developing neutralizing antibody or failed to produce any at all.

Figure 11:
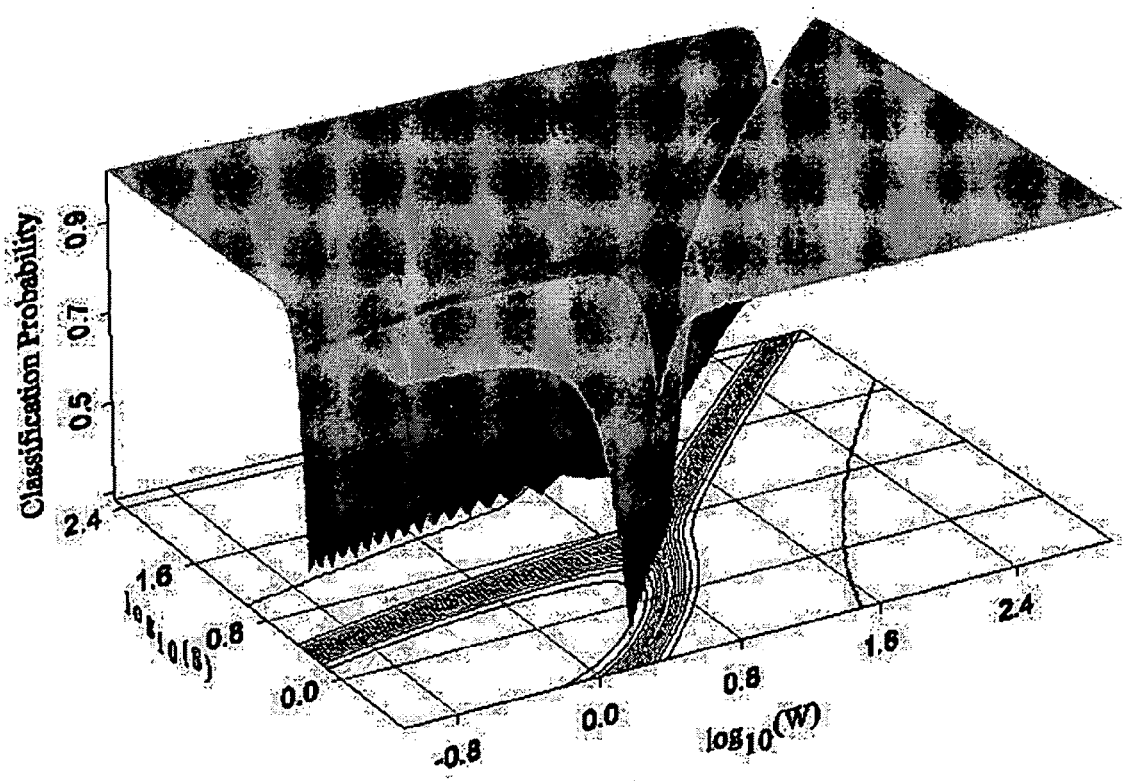
FIG. 11 illustrates an exemplary presentation of results of the exemplary determination of the presence of absence of viral group antibodies of interest in a sample as a classification probability surface.

The QDA determines classification for a given sample by computing the probabilities that the sample should be classified into each group (anti-WN IgM-positive, anti-SLE IgM-positive, and negative) after which the classification is made to the group with the highest probability. The line in FIG. 9 represents the coordinates of $\log_{10}$ (W) and $\log_{10}$ (S) pairs where the group classification probabilities on either side of the line are equal. As the difference between the individual group classification probabilities increases, visualized in FIG. 10 by moving further away from the line, the certainty of correct classification increases. The surface shown in FIG. 11 was made by computing the correct classification probability over a grid of $\log_{10}$ (W) and $\log_{10}$ (S) pairs in the range of the observed data. The contour plot on the $\log_{10}$ (W)-$\log_{10}$ (S) plane is an interpretation of the surface, where contour lines closer together indicate steeper grade on the surface. Samples associated with coordinates $\log_{10}$ (W) and $\log_{10}$ (S) which yield classification probabilities on the plateaus of the surface plot therefore have high probabilities (>95%) of correct classification. The steepness of the canyon walls in the surface reflect the relatively high discriminatory ability of the QDA classification scheme for these data, which in turn reflects the large separation of the $\log_{10}$ (W) and $\log_{10}$ (S) values for the different groups (see FIG. 9).

Serum specimens not included in the QDA were analyzed by the duplex MIA and by MAC-ELISA. The results from the duplex MIA for 351 samples were transformed and classified using the previously generated QDA to provide an independent classification using the duplex MIA. The details of the results are shown in Table 3 below.

TABLE 3

QDA classifications versus MAC-ELISA classifications for samples not used to generate the classification rules.

| MAC-ELISA Classification | QDA Classification | | | |
|---|---|---|---|---|
| | N | SLE | WN | Total |
| NEG | 103 | 1 | 0 | 104 |
| SLE | 11 | 32 | 0 | 43 |
| WN | 8 | 12 | 153 | 173 |
| EQUIVOCAL | 28 | 3 | 0 | 31 |
| TOTAL | 150 | 48 | 153 | 351 |

Not including samples that were found to be equivocal by MAC-ELISA (31/351) the agreement of the duplex MIA compared to the MAC-ELISA was 90% (288/320). The greatest discrepancy between the two methods occurred when one method classified a sample as anti-SLE IgM-positive and the other method classified it as one of the other two groups.

A nonspecific reactor is defined as a sample that reacts with the negative antigen such that the result using the viral antigen cannot be interpreted. In the duplex MIA this situation could produce a false-positive result. Numerically, a nonspecific reaction was defined as follows: For the WN viral antigen, a specimen that had a $\log_{10}$ (W) value <0.857 and a raw MFI value of >8 times the mean value of the negative control sera reacted on the WN viral antigen was considered to have a nonspecific reaction against the negative control recombinant antigen. For the SLE viral antigen a specimen that had a $\log_{10}$ (S) value <0.549 and a raw MFI value of >5 times the mean value of the negative control sera reacted on the SLE viral antigen, was considered to have a nonspecific reaction against the negative control suckling mouse brain antigen. These values corresponded to the lowest values for samples used to generate the QDA classification rules that were classified as anti-WN or anti-SLE IgM-positive (confirmed by PRNT), respectively. The definition was retrospectively applied to all the $\log_{10}$ (W) and $\log_{10}$ (S) values of the specimens included in the QDA. Of the samples with both negative true classifications and negative classifications with the duplex MIA, 6% (12/200) of WN viral antigen reactions and 11% (23/200) of SLE viral antigen reactions were classified as nonspecific. A total of 7.1% (35/491) samples were thus classified as nonspecific reactions. By comparison, rates of nonspecific reactions seen by searching the ADB Diagnostics and Reference Laboratory results database were 2.3% of all WN MAC-ELISA-positive results and 7.0% for SLE MAC-ELISA-positive results.

Twenty-three serum specimens produced nonspecific background reactions with the negative control antigen in the WN MAC-ELISA, the SLE MAC-ELISA or both, but were PRNT-negative (true negative). These samples were tested to determine if similar nonspecific reactions were observed in the duplex MIA. The overall rate of nonspecific reactions among these samples was 26% (6/23).

To test how specific the duplex MIA is in regard to antibodies produced by infections other than WN and SLE viruses, panels were assembled from a variety of sources (see FIG. 8). Results are shown in Table 4 below.

TABLE 4

Human specificity control serum panels tested by WN/SLE duplex MIA.

| Antibody identity | No. of sera | MIA result | | | |
|---|---|---|---|---|---|
| | | WN | SLE | NS[a] | NEG |
| La Crosse encephalitis | 12 | 0 | 0 | 0 | 12 |
| Old flavivirus[b] | 10 | 0 | 0 | 0 | 10 |
| DEN (low IgM)[c] | 15 | 0 | 0 | 1 | 14 |
| DEN (high IgM)[d] | 18 | 1 | 3 | 5 | 9 |
| YF vaccine | 16 | 0 | 0 | 0 | 16 |
| Other arboviruses[e] | 11 | 0 | 0 | 0 | 11 |
| Syphilis | 21 | 1 | 0 | 0 | 20 |
| Antinuclear antibody | 22 | 0 | 0 | 0 | 22 |
| Rheumatoid factor | 13 | 0 | 0 | 1 | 12 |
| Lyme disease (IgM) | 10 | 0 | 0 | 0 | 10 |
| Lyme disease (IgG) | 10 | 0 | 0 | 0 | 10 |
| Negative | 154 | 0 | 0 | 6 | 148 |
| Total | 312 | 2 | 3 | 13 | 294 |

[a]NS nonspecific
[b]Determined by a positive IgG ELISA/negative MAC-ELISA result.
[c]DEN MAC-ELISA P/N >2<9.
[d]DEN MAC-ELISA P/N ≧9.
[e]Included Eastern equine encephalitis, Chikungunya virus, Colorado Tick Fever virus and Jamestown Canyon virus antibodies.

The panels that gave either positive, or nonspecific (according to the definition above) results were the dengue (DEN) (low IgM) (1/14 nonspecific); DEN (high IgM) (1/18 WN; 3/18 SLE; 5/18 nonspecific); Syphilis (1/21 WN); Rheumatoid factor (1/13 nonspecific). Of 154 samples negative by MAC-ELISA to all arboviruses tested for, 6 gave nonspecific results. All other groups were 100% specific.

Thirty-seven serum specimens were subjected to the duplex MIA on different plates and read at different times to determine if the results were reproducible. The QDA classifications agreed for all 37 replicates. The ICC was 0.986 (95% CI 0.974-0.993) for the $\log_{10}$ (W) values and 0.970 (95% CI 0.942-0.984) for the $\log_{10}$ (S) values. A similar study using 40 different serum samples was performed to evaluate within-plate reproducibility. All QDA classifications agreed between the replicates. The ICC for the $\log_{10}$ (W) values was 0.994 (95% CI 0.988-0.997), and for the $\log_{10}$ (S) values was 0.956 (95% CI 0.918-0.976).

The CSF sample results were classified using the QDA classification rules derived using the serum sample set. These were compared to the interpretations in the DVBID database, which were based on MAC-ELISA or PRNT results, or both. The duplex MIA yielded 20 negatives, 3 anti-SLE IgM-positives, and 58 anti-WN IgM-positives. Of the 81 samples, 80 samples had duplex MIA results that were consistent with the previous laboratory results. One sample was incorrectly classified as WN when it should have been negative. Original laboratory results identified it as Powassan IgM-positive, so presumably, flaviviral cross-reactivity was responsible for the incorrect classification.

The transformation of the data from raw MFI values to standardized adjusted values includes three operations that are not addressed in the method used for MAC-ELISA data analysis (e.g., action 701 of method 700). First, all MFI values for viral antigen reactions are adjusted by their respective negative antigen reactions (e.g., action 702 of method 700). This is important when a comparison between antigens is being made, because individual specimens may have different reactions on different negative antigens. Second, differences between anti-WN and anti-SLE IgM-positive controls are adjusted for (e.g., action 704 of method 700). Third, all data are standardized to other plates (a historical standard) so that results are comparable across plates (e.g., action 706 of method 700). The decision was made to force the regression line used in this standardization through the origin based on the fact that negative MFIs do not occur in practice. The assumption is that the controls on a plate reflect what is happening to all the samples on a plate, and, therefore, the effect of an unusual mean control value would be captured by the slope of the standardization regression line, thus permitting sample values on the plate to be corrected.

Table 1 presents the results as "percent correct classification." This term was used as opposed to the term "sensitivity", because the latter refers to a dichotomy consisting generically of a "positive" and a "negative" group. Here there are three groups; therefore percent correct classification avoids ambiguity. The percent correct classifications of the duplex MIA were superior overall to those of the MAC-ELISAs, with the most improvement seen for the anti-SLE IgM-positive group. The percent correct classifications were computed by cross-validation, which involves leaving one data point at a time out of the data set, fitting the QDA to the remainder of the data points, and then classifying the data point in question. This is done for each data point in the set. This is a useful way to assess anticipated predictive performance of the classification algorithm, because it classifies specimens that were not used in the data set used to create the classification rule. This method is superior to "Plug-In" methods, where the sample that is being classified has been used in the construction of the classification rule. Coincidentally, with these data, the correct classification rates for all groups were identical for both methods.

The percent correct classifications reported in this analysis relate primarily to samples taken less than 50 days after onset of symptoms, because this was the specimen set available. The duplex MIA and the MAC-ELISA both have high correct classification percents for anti-WN IgM-positive samples and negative samples. From this information it can be extrapolated that anti-WN IgM is detected with similar accuracy by the duplex MIA in samples from 0-50 days after onset of symptoms. Only six samples were obtained >50 days past onset of symptoms, and so a precise statement about the anticipated performance of the duplex MIA cannot be made for such samples.

The specificity data identified two groups of samples having results of particular interest when tested in the WN/SLE duplex MIA. The DEN (high IgM) category gave 4/18 results that were either positive for WN- or SLE IgM or both, and five that gave nonspecific results. The same 18 samples were analyzed by WN and SLE MAC-ELISA (data not shown), with 11/18 being positive for WN- or SLE IgM or both. A further five samples were equivocal or nonspecific. Flaviviruses exhibit significant cross-reactivity with one another and therefore these results are unsurprising; however, results suggest that the MIA may be less prone to generation of positive results for samples containing DEN antibodies than the MAC-ELISAs. The addition of DEN to the QDA analysis may provide for easier discrimination between primary flaviviral infections; the anamnestic responses seen with some secondary flaviviral infections would likely confound the picture, however. None of the cross-reactors tested positive by WN PRNT. Here, specificity data revealed one sample containing anti-syphilis antibodies that gave a positive reaction to WN in the MIA. This result was confirmed using the WN MAC-ELISA and also by PRNT (WN 1:1280; SLE 1:40). This indicated that the patient was carrying antibodies from a co-infection. Further clinical information or follow-up specimens were unavailable, but the patient was known to be resident in an area experiencing WN virus activity.

The criteria used to identify samples that reacted nonspecifically with negative antigen were necessarily different from those used in the MAC-ELISA, which are directed at positive results. In the MIA, false-negatives could potentially exist because nonspecific reactions with the negative control antigen could generate artificially low numbers in the first action of the data transformation scheme. The criteria to define a nonspecific reaction presented here are quite stringent, and are based purely on the data set under evaluation. As more experience is gained with the duplex MIA these criteria may be modified. The samples that were identified retrospectively as having nonspecific reactions to either of the negative control antigens remained an integral part of the QDA. Removal of these samples would have marginally improved the reported correct classification rates, but the practical effects would be negligible. Conversely, the inclusion of these samples improved the robustness of the analysis, particularly of the SLE component.

The initial analysis of the duplex MIA by using samples not used in the derivation of the duplex MIA classification rules is shown in Table 3. To get a more accurate indication of performance of the test where results fall close to the QDA classification boundaries, samples with a maximum absolute difference in classification probabilities of <80% are currently being analyzed by WN and SLE virus PRNT, and this cut-off may later be revised if necessary. The duplex MIA results, however, will not be reported as equivocal because such a result does not help in diagnosis.

Results from the WN/SLE duplex MIA will be interpreted as follows: Classification of a sample as WN or SLE viral IgM-positive will indicate a presumptive infection with that virus; negative will indicate an absence of anti-viral IgM to either virus; nonspecific will indicate either that the results could not be differentiated or that background reactions on the negative antigen inhibited interpretation, and that a different test should be performed.

The classification of the CSF samples using the QDA classification rules generated by the serum specimens appeared to be successful despite the fact that ideally we would have developed CSF classification criteria using CSF data in a QDA.

Example 16

Exemplary Application to Dengue Virus

Table 5 shows a summary of microsphere-based immunoassay results for the dengue virus (DEN). The numbers shown represent an observed fluorescent intensity for a particular DEN antigen divided by the negative antigen observed fluorescent intensity. In the example, the antibody 6B6C-1 was used as a capture agent.

In the example, antigens of all four DEN serotypes were used. The results indicate that a multiplex microsphere-based immunoassay with another flavivirus is possible. Such an approach can have the same benefits (e.g., vis-à-vis ELISA) as the other multiplex scenarios described herein.

Most, but not all antisera reacted the best on the DEN 3 preparation. A single serio type of DEN can be used. Alternatively, more than one (e.g., all four) could be used to optimize results.

TABLE 5

Summary of Results anti-dengue (aDEN) sera.

| Sample | DEN 1 antigen | DEN 2 antigen | DEN 3 antigen | DEN 4 antigen |
|---|---|---|---|---|
| aDEN1 #1 | 186.5 | 74.9 | 137.0 | 46.5 |
| aDEN1 #2 | 57.4 | 56.1 | 62.7 | 38.0 |
| aDEN1 #3 | 66.9 | 20.6 | 54.4 | 19.3 |
| aDEN1 #4 | 55.1 | 8.6 | 30.9 | 7.9 |
| aDEN1 #5 | 7.6 | 14.3 | 15.7 | 5.0 |
| aDEN1 #6 | 34.6 | 16.3 | 64.9 | 6.9 |
| aDEN1 #7 | 299.7 | 155.1 | 286.1 | 53.2 |
| aDEN1 #8 | 37.8 | 20.6 | 34.9 | 3.1 |
| aDEN2 #1 | 5.2 | 5.8 | 5.2 | 5.7 |
| aDEN2 #2 | 122.0 | 137.6 | 70.5 | 99.3 |
| aDEN2 #3 | 18.9 | 13.3 | 13.8 | 11.6 |
| aDEN2 #4 | 21.7 | 17.7 | 16.4 | 14.7 |
| aDEN2 #5 | 38.7 | 26.4 | 30.8 | 18.3 |
| aDEN2 #6 | 27.3 | 21.6 | 39.7 | 19.6 |
| aDEN2 #7 | 64.0 | 20.1 | 47.0 | 42.3 |
| aDEN2 #8 | 809.8 | 304.3 | 912.8 | 14.5 |
| aDEN3 #1 | 30.8 | 32.8 | 29.1 | 21.0 |
| aDEN3 #2 | 16.1 | 0.6 | 56.0 | 4.0 |
| aDEN3 #3 | 85.9 | 36.8 | 85.6 | 20.6 |
| aDEN3 #4 | 5.9 | 3.0 | 30.8 | 3.7 |
| aDEN3 #5 | 11.7 | 7.9 | 27.8 | 4.7 |
| aDEN3 #6 | 24.6 | 10.3 | 45.2 | 1.7 |
| aDEN3 #7 | 108.8 | 44.2 | 413.7 | 28.0 |
| aDEN3 #8 | 16.9 | 8.1 | 48.0 | 0.9 |
| aDEN4 #1 | 21.8 | 14.7 | 34.2 | 8.8 |
| aDEN4 #2 | 12.2 | 17.4 | 15.4 | 10.4 |
| aDEN4 #3 | 21.5 | 30.2 | 18.1 | 19.8 |
| aDEN4 #4 | 8.0 | 9.1 | 10.8 | 6.5 |
| aDEN4 #5 | 9.2 | 20.2 | 13.6 | 9.6 |
| aDEN4 #6 | 2.6 | 3.1 | 3.4 | 2.4 |
| aDEN4 #7 | 4.2 | 3.3 | 5.8 | 4.6 |
| aDEN4 #8 | 88.6 | 42.8 | 530.3 | 8.8 |
| Mean | 72.6 | 37.4 | 99.7 | 17.5 |

Example 17

Exemplary Use of Monoclonal Antibody as Substitute for Positive Serum Controls

In the dengue scenario described above, an antibody (e.g., 4G2-PE) was used as a proposed substitute for positive serum controls and reacted on all four serotypes (best on DEN 1 and DEN 4). Thus, the results indicate that such an antibody can be used in place of positive sera controls in any of the examples described herein (e.g., for any microsphere-based immunoassay involving flaviviruses). The same principle may be used for MIAs for other arboviruses (e.g., MAb 2A2C-3 may be used as a positive control for alphavirus tests).

Example 18

Exemplary Inclusion of Negative Antigens with Viral Antigens in Single Well

A microsphere-based immunoassay was performed in which the negative antigens were included with the viral antigens in a single well. The ratios of the controls and backgrounds (e.g., negative antigen reactions) observed were sufficiently similar to indicate that such an approach can work for any of the examples described herein. For example, the West Nile/SLE microsphere-based immunoassay can use a single well with four different bead sets (e.g., one for West Nile viral, one for SLE viral, one for West Nile negative antigen, and one for SLE negative antigen). The approach can also be applied to other (e.g., arboviral) tests, such as EEE and DEN 1-4 when added into the multiplex.

The advantage of such an approach is that fewer wells (e.g., half the number of wells) can be used, and less reagent can also be used. Also, the test can be faster because it takes less time (e.g., half) to count the results.

Example 19

Exemplary Application to Eastern Equine Encephalitis Virus

A microsphere-based immunoassay was performed for detection of eastern equine encephalitis (EEE) virus. The results indicated that the forty-one (41) samples identified as positive by EEE MAC-ELISA (Positive/Negative >3 and confirmed by PRNT) were also identified as positive by EEE IgM microsphere-based immunoassay (MFI>=400) as shown in FIG. 12.

Figure 12:
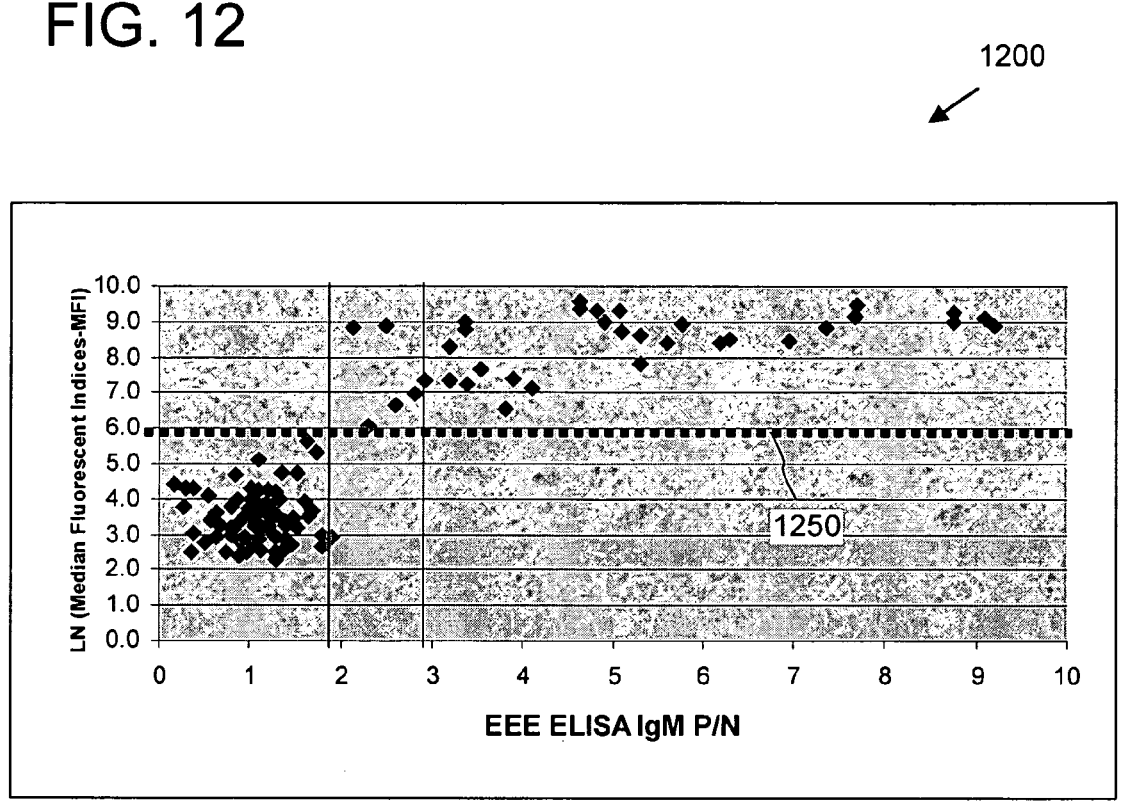
FIG. 12 illustrates exemplary results of MIA detection done for eastern equine encephalitis (EEE).

In FIG. 12, the chart 1200 shows comparison of classification for ELISA (x-axis) and MIA (y-axis). ELISA results are expressed as Positive/Negative (P/N), and MIA results are expressed as natural log of the MFI (LN of MFI). The line 1250 represents an MFI of 400 (the natural log of 400 equals 5.99), which was used as a threshold.

In the example, six (6) equivocal samples by MAC-ELISA (P/N 2-3) were identified as positive by IgM MIA (MFI>=400) as shown in FIG. 12. Eighty-two (82) negative serum samples by MAC-ELISA (P/N<2) were identified as negative in the IgM MIA (MFI<400). In addition, 104 other arbovirus positive samples tested negative in the IgM MIA, indicating specificity of at least 95 percent.

Advantages of the MIA include reduced testing turnaround time. Forty samples can be tested in approximately 4 hours; ELISA takes about 2 days for the same number of samples). Also less hands-on technician time is required: between 1.0 to 1.5 hours for 40 samples for MIA; ELISA takes about 2.0-2.5 hours. The IgM MIA is as specific as the MAC-ELISA technique. The IgM MIA is slightly more sensitive than the MAC-ELISA technique.

In the example, microsphere set 15 (from Luminex Corporation) was coupled to purified alphavirus cross-reactive (e.g., EEE, WEE, and VEE) MAb 2A2C-3. The coupled microspheres were divided and EEE virus suckling mouse brain (SMB) antigen was added to half, and normal SMB antigen was added to the remaining half.

Serum samples and controls were IgG depleted using protein G and then diluted 1:400. CSF samples were tested without IgG depletion (diluted 1:5).

EEE SMB and normal SMB microspheres were added to a 96-well filter plate. The plates were vacuumed and washed. Phycoerythrin-conjugated donkey anti-human IgM was added to all wells. Diluted samples were added to wells containing EEE SMB microspheres and to wells containing normal SMB microspheres. The contents of the wells were mixed, and the plates were shaken for 1.5 hours.

The results indicate that EEE virus detection can be accomplished in a multiplex scenario by using a distinguishable microsphere set in conjunction with other virus detection as described herein.

Example 20

Exemplary Application to Other Isotypes

Although some examples herein are directed to detection of the IgM antibody isotype, an approach aimed at detecting other isotypes can also be employed. For example, Table 6 shows an example detecting the IgG isotype in a duplex scenario involving both Saint Louis encephalitis and West Nile virus. In the example, Em indicates an IgM ELISA result; Eg indicates and IgG ELISA result, Nt indicates PRNT results. MFI results are obtained via an MIA technique as described herein (e.g., a multiplex MIA).

TABLE 6

Excerpt of Dataset for IgG Technique

| R # | Em.SLE | Em.WN | Eg.SLE | Eg.WN | Nt. SLE | Nt. WN | IgG WN MFI | IgG SLE MFI | IgM Classify Result | Days post onset |
|---|---|---|---|---|---|---|---|---|---|---|
| 1 | 0.88 | 11 | 8.6 | 19.8 | 20 | 5120 | 3463 | 1331 | WN | 0 |
| 2 | 1.1 | 5.3 | 11.2 | 11.4 | 20 | 5120 | 185 | 114.5 | Nonspecific | 9 |
| 3 | 1.3 | 4.5 | 0.92 | 0.82 | <10 | <10 | 65 | 32 | Neg | 1 |
| 4 | 1.7 | 13 | 10 | 11.6 | 20 | 640 | 732 | 717 | Nonspecific | 37 |
| 5 | 1.2 | 3.3 | 19.8 | 16.6 | 80 | 2560 | 62 | 163 | Nonspecific | 30 |
| 6 | 1.5 | 9.7 | 16.5 | 11.4 | 160 | 320 | 1013 | 2839 | SLE | 10 |
| 7 | 1.3 | 3.7 | * | 4 | <10 | 80 | 36 | 55 | Nonspecific | 5 |
| 8 | 2.3 | 11.3 | 4.3 | 4.7 | 10 | 80 | 465.5 | 211 | Nonspecific | 5 |
| 9 | 1.3 | 3.5 | 3 | 7.5 | | | 900 | 277.5 | WN | 55 |
| 10 | 1.3 | 7.3 | 13.4 | 13.6 | 80 | 80 | 1199.5 | 2743 | SLE | 10 |
| 11 | 5.4 | 1.3 | 1.8 | 1.8 | <10 | <10 | 23 | 15 | Neg | 20 |
| 12 | 3.4 | 1.2 | * | * | <10 | <10 | 23 | 17 | Neg | 100 |
| 13 | | 1.3 | | 11.3 | 160 | 20‡ | 1787.5 | 2650.5 | SLE | 2 |
| 14 | | | | | 2560 | 320‡‡ | 2472 | 4058 | SLE | 6 |
| 15 | 6.5 | 4.7 | 16.1 | 14.2 | >20,480 | >20,480 | 3352 | 7033.5 | SLE | 0 |
| 16 | 3.2 | 2.6 | 2.4 | 4.4 | 40 | 640 | 1318 | 279 | WN | 3 |
| 17 | 2.3 | 4.5 | 9.7 | 7.2 | 20 | 40 | 1548 | 3621 | SLE | 0 |
| 18 | .98 | 2.5 | 3.5 | 4.5 | 20 | 160 | 1165 | 561.5 | Nonspecific | 332 |
| 19 | 1.9 | 10.5 | 1.2 | 1.7 | 10 | 1280 | 351.5 | 769.5 | SLE | 8 |
| 20 | 2.0 | 4.5 | 6.8 | 6.5 | 10 | 20 | 529 | 1096 | SLE | 7 |
| 21 | 1.0 | 2.6 | 7.7 | 11.7 | 20 | 320 | 95.5 | 60 | Nonspecific | 32 |
| 22 | 1.7 | 1.0 | .88 | .94 | <10 | <10 | 28 | 40.5 | Neg | |
| 23 | 1.0 | 1.0 | .97 | 1.0 | <10 | <10 | 98 | 204 | Nonspecific | |
| 24 | 1.4 | 5.5 | 6.3 | 11.2 | 10 | 320 | 332.5 | 101 | Nonspecific | 22 |
| 25 | 4.5 | 19.2 | .70 | 1.3 | <10 | 20 | 167 | 25 | Nonspecific | 3 |
| 26 | 4.2 | 22.7 | 4.6 | 9.6 | 20 | 5120 | 4705 | 1021 | WN | 25 |
| 27 | 3.7 | 3.7 | 17.5 | 11.1 | 2560 | 2560 | 3364 | 6392 | SLE | 16 |
| 28 | 4.3 | .92 | .76 | .66 | <10 | <10 | 12 | 16 | Neg | 10 |
| 29 | 2.9 | 1.2 | 1.8 | 1.2 | <10 | <10 | 12 | 11 | Neg | 33 |
| 30 | 3.0 | 2.3 | 1.8 | 1.5 | <10 | <10 | 28 | 31 | Neg | 22 |
| 31 | 1.9 | 1.5 | 8.1 | 8.8 | 80 | 2560 | 1642 | 448 | WN | 14 |
| 32 | 6.4 | 7.7 | 14.5 | 5.0 | 1280 | 1280 | 1198.5 | 2897.5 | SLE | 6 |
| 33 | .81 | .87 | 2.1 | 1.0 | 10 | <10 | 24.5 | 89 | Nonspecific | |
| 34 | 1.3 | 1.1 | 5.6 | 3.7 | 40 | <10 | 129 | 447 | SLE | |
| 35 | 1.7 | 1.1 | 5.2 | 1.5 | 40 | 10 | 53.5 | 917.5 | SLE | |
| 36 | | | | | 40 | 160‡‡‡ | 2334 | 4345.5 | SLE | 27 |
| 37 | 1.3 | 1.2 | 5.2 | 3.5 | 10 | <10 | 75 | 254 | Nonspecific | |
| 38 | 5.2 | 4.7 | 6.1 | 6.4 | 10 | 10‡‡‡‡ | 767 | 1638 | SLE | 0 |
| 39 | | | | | 20 | 10 | 1825.5 | 2889.5 | SLE | |
| 40 | | | 4.5 | 2.4 | 40 | 20 | 47 | 362 | SLE | 73 |

‡Nt. DEN value of 5120
‡‡Nt. DEN value of >81,920
‡‡‡Nt. DEN value of 2560
‡‡‡‡Nt. DEN value of 80

The method for the IgG MIA is much the same as that for the IgM MIA. Differences include that the sera do not need to be depleted of IgG, and the conjugate is IgG-PE instead of IgM-PE. Table 7 indicates a Summary of the results for the MIA.

TABLE 7

Summary of MIA results for IgG Technique

| Summ. | IgG WN MFI | IgG SLE MFI |
|---|---|---|
| WN pos | 1648 | 640 |
| SLE pos | 777 | 1736 |
| Normal | 11 | 10 |
| Normal | 12 | 9 |

The MFI data of the IgG results were evaluated with the automated classification technique described herein for IgM. Because cross-reactivity among flaviviruses in IgG antibody tests is expected and observed, the classification technique can be modified to reflect such cross-reactivity. In cases in which SLE and WN cannot be distinguished in the IgG MIA, the results can indicate simply a "flavivirus" designation. The technique can also be changed to reflect different classification parameters (e.g., based on quadratic discriminant analysis or another method) to differentiate the WN and SLE cases.

In the example, there is a clear delineation between positive and negative MFIs, as well as a difference in the MFIs of true SLE and true WN positives. The method can be a good adjunct to the IgM MIA. Having access to IgG data can be useful in various situations (e.g., to indicate that person was infected with virus years ago or the like) to give a clearer picture for purposes of diagnosis.

Example 21

Exemplary Automated Classification Techniques

In any of the examples herein, classification can be performed by automated means, such as a computer program. For example, a spreadsheet (e.g., using the MICROSOFT EXCEL spreadsheet format) including an add-in (e.g., a macro) can be used.

As described herein, such an automated classification technique can take fluorescent intensities or indices as input and output a simple designation as results indicating whether the sample tends to indicate that the person is infected with a particular virus. For example, the simple designation can indicate the name of the virus (e.g., "West Nile," "SLE," or the like) for a positive result, a negative result (e.g., "Negative"), or a result that informs the reader that further tests are indicated (e.g., a nonspecific infection such as "Nonspecific" or a preliminary outcome such as "confirm SLE").

Such an approach can be helpful in guiding the diagnosis process. The technique can be implemented by computer-executable instructions (e.g., symbolic instructions to be executed by a microprocessor) stored on one or more computer-readable media (e.g., magnetic media, optical media, or memory).

Although the result may appear to be simple, the calculations required to generate such a simple result can employ any number of the techniques described herein, such as the normalization and quadratic discriminant techniques.

Example 22

Exemplary Automated Classification Program

Automated analysis can be accomplished by accepting input showing results from a flow instrument in an MIA scenario for one or more samples as described herein. For example, the BIO-PLEX instrument includes accompanying software that can generate an .RBX file that can be converted to a spreadsheet (e.g., a workbook). Information in the spreadsheet can be processed according to the techniques described herein (e.g., taking controls into account in conjunction with normalization and quadratic discriminant analysis) and output a result for each sample. Output results can include the virus name if the result is positive for a particular virus (e.g., "SLE, "WN," or the like), an indication of a negative result (e.g., "Neg" or the like), or a result showing that further tests are indicated (e.g., "Nonspecific" or the like).

The result showing that further tests are indicated can be shown in various scenarios. If desired, further information (e.g., output identifying the particular scenario) can be indicated in the spreadsheet. For example, further tests can be indicated due to background reaction of a specimen on the negative control antigen, two or more positive classifications (e.g., for two or more different, specific antibodies) that are too close to conclusively distinguish, or a positive that is considered too low to be a conclusive positive.

An example of a positive that is considered too low is analogous to a MAC-ELISA situation involving a Positive/Negative of between 2.0-2.9. However, in the MIA situation, analysis can be determined based on parameters outside of the confirmed positives. The cutoffs can be applied after various manipulations that take into account the antigen and serum controls, standardization to historical values, and the like.

In some cases, additional testing may be indicated, even if the output is a positive result. For example, in a scenario involving insufficient positive samples available for independent validation (e.g., for a particular virus type), additional testing may be desirable.

An example of a computer program implementing such a technique is shown in the "MIAClassify" MICROSOFT EXCEL add-in included in the computer program listing appendix. The add-in can be implemented as a macro that appears under the "Tools" menu. Alternatively, the computer program can be implemented as a stand alone program or web-based service.

Example 23

Exemplary Advantages and Applications of Technologies

The speed at which these tests can be performed and the ability to multiplex make this methodology particularly attractive to the detection and classification of multiple viral infections of the same viral group in a single assay. MIAs can be especially applicable for testing for infection of viruses of the same genus which share similar formats (e.g., arboviruses), by assembling microparticles using the same viral group-reactive antibody. In any of the examples herein, the viral group-reactive antibody can react with any of a variety of viruses within a viral group. For example, an implementation detecting both West Nile and Saint Louis encephalitis can use an arbovirus group-reactive antibody. Thus, in the example described herein, the first antibody of interest can be that corresponding to West Nile, and the second antibody of interest can be corresponding to Saint Louis encephalitis (or vice-versa). Other combinations are possible.

Furthermore, the volume of CSF necessary for testing in the duplex MIA is only ⅕ of the volume needed in the MAC-ELISAs, a significant advantage because of the limited volume of CSF that is often received. Another important factor is the decreased turnaround time for the duplex MIA (approximately 4.5 hours) as opposed to the MAC-ELISAs (2 days). The ability to compare results from different runs and/or labs directly with each other when similar controls are used is now possible by using the described analysis. Such comparison is not possible with the MAC-ELISAs currently in use. Additionally, the use of different antigen lots or different test performances among labs should be accounted for by the data transformations. The use of a capture system whereby antigen is captured on to MAb-coated microspheres allows for the use of different antigen preparation methods, so that very pure antigens are not required for the test to function. Thus, positive identification of IgM to viral genuses other than flaviviruses, such as alphaviruses and bunyaviruses, can occur using other coating antibodies on the microparticles. The ability to classify additional anti-viral reactions can be successful using a multiplex assay according to the method described. In addition, tests to measure other immunoglobulin classes (for example, IgG and IgA) can be designed based on the same assay format, with the substitution of the anti-human IgM PE for other anti-human Ig classes labeled with PE (for example, IgG PE and IgA PE).

Example 24

Exemplary Computational Biology Methods for Differentiating Groups of Data

There are a wide variety of clustering and classification methods used in computation biology to differentiate data into distinct classes. As described herein, the classification method used is quadratic discriminant analysis (QDA) but any computational biology method for differentiating groups of data can be used. Other potential methods included a) mean+/−3× standard deviation; b) 3-way receiver operator characteristic analysis; c) and linear discriminant analysis. The QDA was the most flexible in that it optimized group sensitivities, considered the results simultaneously, and admitted different variances and correlations for the groups, a combination of which could not be achieved via the other methods.

Clustering (or cluster analysis) is unsupervised learning where the classes are unknown a priori and the goal is to discover these classes from data. For example, the identification of new tumor classes using gene expression profiles is a form of unsupervised learning.

Classification (or class prediction) is a supervised learning method where the classes are predefined and the goal is to understand the basis for the classification from a set of labeled objects and build a predictor for future unlabeled observations. For example, the classification of malignancies into known classes is a form of supervised learning.

An overview of classification computational methods is provided below.

CLASSIFICATION

There is old and extensive literature on classification, at least in statistics, machine learning, and psychometrics. Examples of classifiers include logistic regression, discriminant analysis (linear and quadratic), principle component analysis (PCA), nearest neighbor classifiers (k-nearest neighbor), classification and regression trees (CART), prediction analysis for microarrays, neural networks and multinomial log-linear models, support vector machines, aggregated classifiers (bagging, boosting, forests), and evolutionary algorithms.

Logistic Regression

Logistic regression is a variation of linear regression which is used when the dependent (response) variable is a dichotomous variable (i.e., it takes only two values, which usually represent the occurrence or non-occurrence of some outcome event, usually coded as 0 or 1) and the independent (input) variables are continuous, categorical, or both. For example, in a medical study, the patient survives or dies, or a clinical sample is positive or negative for a certain viral antibody.

Unlike ordinary regression, logistic regression does not directly model a dependent variable as a linear combination of dependent variables, nor does it assume that the dependent variable is normally distributed. Logistic regression instead models a function of the probability of event occurrence as a linear combination of the explanatory variables. For logistic regression, the function relating the probabilities to the explanatory variables in this way is the logistic function, which has a sigmoid or S shape when plotted against the values of the linear combination of the explanatory variables.

Logistic regression is used in classification by fitting the logistic regression model to data and classifying the various explanatory variable patterns based on their fitted probabilities. Classifications of subsequent data are then based on their covariate patterns and estimated probabilities.

Discriminant Analysis

In summary discriminant analysis represents samples as points in space and then classifies the points. Linear discriminant analysis (LDA) finds an optimal plane surface that best separates points that belong to two classes. Quadratic discriminant analysis (QDA) finds an optimal curved (quadratic) surface instead. Both methods seek to minimize some form of classification error.

Fisher Linear Discriminant Analysis (FLDA or LDA)

LDA finds linear combinations (discriminant variables) of data with large ratios of between-groups to within-groups sums of squares and predicts the class of an observation x by the class whose mean vector is closest to x in terms of the discriminant variables. Advantages of LDA include that it is simple and intuitive where the predicted class of a test case is the class with the closes mean and it is easy to implement with a good performance in practice. Disadvantages of LDA Include the Following:
1. linear discriminant boundaries may not be flexible enough
2. features may have different distributions within classes
3. in the case of too many features, performance may degrade rapidly due to over parameterization and high variance of parameter estimates.

Nearest Neighbor Classifiers

Nearest neighbor methods are based on a measure of distance between observations, such as the Euclidean distance or one minus the correlation between two data sets. K-nearest neighbor classifiers work by classifying an observation x as follows:

find the k observations in the learning set that are closest to x predict the class of x by majority vote, i.e., choose the class that is most common among these k neighbors. Simple classifiers with k=1 can generally be quite successful. A large number of irrelevant or noise variables with little or no relevance can substantially degrade the performance of a nearest neighbor classifier.

Classification Trees

Classification trees can be used, for example, to split a sample into two sub-samples according to some rule (feature variable threshold). Each sub-sample can further split, and so on. Binary tree structured classifiers are constructed by repeated splits of subsets (nodes) into two descendant subsets. Each terminal subset of the tree is assigned a class label and the resulting partition corresponds to the classifier. The three main aspects of tree construction include selection of splits (at each node, the split that maximize the decrease in impurity is chosen), decision to declare a node terminal or to continue splitting (to grow a large tree, the tree is selectively pruned upwards getting a decreasing sequence of subtrees), and assignment of each terminal node to a class (the class the minimizes the resubstitution estimate of the misclassification probability is chosen for each terminal node).

Prediction Analysis for Microarrays

These methods utilize nearest shrunken centroid methodology. First, a standardized centroid for each class is computed. Then each class centroid is shrunk toward the overall centroid for all classes by the so-called threshold (chosen by the user). Shrinkage consists of moving the centroid towards zero by threshold, setting it equal to zero if it hits zero.

Artificial Neural Networks

The key element of the artificial neural network (ANN) model is the novel structure of the information processing system. It is composed of many highly interconnected processing elements that are analogous to neurons and are tied together with weighted connections that are analogous to synapses. As with all classification methods, once the ANN is trained on known samples, it will be able to predict samples automatically.

Support Vector Machines

Support Vector Machines are learning machines that can perform binary classification (pattern recognition) and real valued function approximation (regression estimation) tasks. Support Vector Machines non-linearly map their n-dimensional input space into a higher dimensional feature space. In this high dimensional feature space a linear classifier is constructed.

Aggregating Classifiers

This method works by aggregating predictors built from perturbed versions of a learning set. In classification, the multiple versions of the predictor are aggregated by voting. Bootstrapping is the simplest form of bagging in which perturbed learning sets of the same size as the original learning set are non-parametric bootstrap replicates of the learning set, i.e., drawn at random with replacement from the learning set. Parametric bootstrapping involves perturbed learning sets that are generated according to a mixture of multivariate Gaussian distributions. Random Foresting is a combination of tree classifiers (or other), where each tree depends on the value of a random vector for all trees in the forest. In boosting, classifiers are constructed on weighted version the training set, which are dependent on previous classification results. Initially, all objects have equal weights, and the first classifier is constructed on this data set. Then, weights are changed according to the performance of the classifier. Erroneously classified objects get larger weights, and the next classifier is boosted on the reweighted training set. In this way, a sequence of training sets and classifiers is obtained, which is then combined by simple majority voting or by weighted majority voting in the final decision.

Example 25

Exemplary Computer System for Conducting Analysis

FIG. 13 and the following discussion provide a brief, general description of a suitable computing environment for the software (for example, computer programs) described above. The methods described above can be implemented in computer-executable instructions (for example, organized in program modules). The program modules can include the routines, programs, objects, components, and data structures that perform the tasks and implement the data types for implementing the techniques described above.

While FIG. 13 shows a typical configuration of a desktop computer, the technologies may be implemented in other computer system configurations, including multiprocessor systems, microprocessor-based or programmable consumer electronics, minicomputers, mainframe computers, and the like. The technologies may also be used in distributed computing environments where tasks are performed in parallel by processing devices to enhance performance. For example, tasks can be performed simultaneously on multiple computers, multiple processors in a single computer, or both. In a distributed computing environment, program modules may be located in both local and remote memory storage devices. For example, code can be stored on a local machine/server for access through the Internet, whereby data from assays can be uploaded and processed by the local machine/server and the results provided for printing and/or downloading.

The computer system shown in FIG. 13 is suitable for implementing the technologies described herein and includes a computer 1320, with a processing unit 1321, a system memory 1322, and a system bus 1323 that interconnects various system components, including the system memory to the processing unit 1321. The system bus may comprise any of several types of bus structures including a memory bus or memory controller, a peripheral bus, and a local bus using a bus architecture. The system memory includes read only memory (ROM) 1324 and random access memory (RAM) 1325. A nonvolatile system (for example, BIOS) can be stored in ROM 1324 and contains the basic routines for transferring information between elements within the personal computer 1320, such as during start-up. The personal computer 1320 can further include a hard disk drive 1327, a magnetic disk drive 1328, for example, to read from or write to a removable disk 1329, and an optical disk drive 1330, for example, for reading a CD-ROM disk 1331 or to read from or write to other optical media. The hard disk drive 1327, magnetic disk drive 1328, and optical disk 1330 are connected to the system bus 1323 by a hard disk drive interface 1332, a magnetic disk drive interface 1333, and an optical drive interface 1334, respectively. The drives and their associated computer-readable media provide nonvolatile storage of data, data structures, computer-executable instructions (including program code such as dynamic link libraries and executable files), and the like for the personal computer 1320. Although the description of computer-readable media above refers to a hard disk, a removable magnetic disk, and a CD, it can also include other types of media that are readable by a computer, such as magnetic cassettes, flash memory cards, DVDs, and the like.

A number of program modules may be stored in the drives and RAM 1325, including an operating system 1335, one or more application programs 1336, other program modules 1337, and program data 1338. A user may enter commands and information into the personal computer 1320 through a keyboard 1340 and pointing device, such as a mouse 1342. Other input devices (not shown) may include a microphone, joystick, game pad, satellite dish, scanner, or the like. These and other input devices are often connected to the processing unit 1321 through a serial port interface 1346 that is coupled to the system bus, but may be connected by other interfaces, such as a parallel port, game port, or a universal serial bus (USB). A monitor 1347 or other type of display device is also connected to the system bus 1323 via an interface, such as a display controller or video adapter 1348. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing data related to determining the presence or absence of viral group antibodies of interest in a sample are possible. For example, the data can be collected and analyzed, and the results presented on different computer systems as appropriate. In addition, various software aspects can be implemented in hardware, and vice versa.

Example 26

Exemplary Computer-Implemented Methods

Any of the computer-implemented methods described herein can be performed by software executed by software in an automated system (for example, a computer system). Fully-automatic (for example, without human intervention) or semi-automatic operation (for example, computer processing assisted by human intervention) can be supported. User intervention may be desired in some cases, such as to adjust parameters or consider results.

Such software can be stored on one or more computer-readable media comprising computer-executable instructions for performing the described actions.

Alternatives

Having illustrated and described the principles of the invention in exemplary embodiments, it should be apparent to those skilled in the art that the described examples are illustrative embodiments and can be modified in arrangement and detail without departing from such principles. Techniques from any of the examples can be incorporated into one or more of any of the other examples.

In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

We claim:

1. A computer-implemented method for determining presence or absence of anti-viral antibodies of interest in a sample comprising:
   receiving data indicating at least one characteristic classification parameter that distinguishes microparticles each having bound thereto a viral group-reactive antibody from other microparticles each having bound thereto the viral group-reactive antibody;
   classifying microparticles based on at least one characteristic classification parameter;
   receiving data in a flow instrument indicating presence or absence of a labeled reagent associated with the classified microparticles, wherein the labeled reagent is bound to the anti-viral antibodies of interest, wherein the data received in the flow instrument is obtained by using a set of microparticles to which a viral group-reactive antibody is covalently bound, wherein the viral group-reactive antibody is reactive to a plurality of viruses within a virus group, wherein a subset of the viral group-reactive antibody is bound to a first specific viral antigen and a subset of the viral group-reactive antibody is bound to a second specific viral antigen, wherein the set of microparticles is combined with a sample comprising antibodies, and wherein a labeled reagent detects binding of the anti-viral antibodies of interest from the sample to the first specific viral antigen or the second specific viral antigen bound to the viral group-reactive antibody covalently bound to the microparticle; and
   determining presence or absence of anti-viral antibodies of interest in the sample based on the data indicating the presence or absence of the labeled reagent associated with the classified microparticles, wherein the method is performed on a suitably programmed computer.

2. One or more computer-readable storage media having computer executable instructions for performing a method for determining presence or absence of anti-viral antibodies of interest in a sample comprising:
   receiving data in a flow instrument indicating at least one characteristic classification parameter that distinguishes microparticles having a viral group-reactive antibody from other microparticles having the viral group-reactive antibody;
   classifying microparticles based on the at least one characteristic classification parameter;
   receiving data indicating presence or absence of a labeled reagent associated with the classified microparticles, wherein the labeled reagent is bound to the anti-viral antibody of interest, wherein the data received in the flow instrument is obtained by using a set of microparticles to which a viral group-reactive antibody is covalently bound, wherein the viral group-reactive antibody is reactive to a plurality of viruses within a virus group, wherein a subset of the viral group-reactive antibody is bound to a first specific viral antigen and a subset of the viral group-reactive antibody is bound to a second specific viral antigen, wherein the set of microparticles is combined with a sample comprising antibodies, and wherein a labeled reagent detects binding of anti-viral antibodies of interest from the sample to the first specific viral antigen or the second specific viral antigen; and determining presence or absence of anti-viral antibodies of interest in the sample based on the data indicating the presence or absence of the labeled reagent associated with the classified microparticles.

3. The computer-implemented method of claim 1, wherein the determining the presence or absence of anti-viral antibodies of interest comprises quadratic discriminant analysis.

4. The computer-implemented method of claim 1, wherein the at least one characteristic classification parameter that distinguishes microparticles comprises at least one parameter selected from the group consisting of:
particle fluorescence emission intensity;
particle color; and
particle size.

5. The computer-implemented method of claim 1, wherein the received data indicating the presence or absence of the labeled reagent associated with the classified microparticles comprises:
data indicating the presence of labeled reagent in microparticles comprising a viral antigen bound to the viral group-reactive antibody and the anti-viral antibodies of interest;
data indicating the presence of labeled reagent in microparticles pretreated with a negative control antigen; and
data indicating the presence of labeled reagent in microparticles comprising a viral antigen bound to the viral group-reactive antibody and a positive control antibody.

6. The computer-implemented method of claim 5, wherein determining the presence or absence of anti-viral antibodies of interest based on the data indicating the presence or absence of the labeled reagent associated with the classified microparticles comprises:
adjusting the received data to account for antigen reactions;
normalizing the received data to account for positive control reactions;
calibrating the received data to standardize across multiple plates; and
classifying the data to represent the presence or absence of anti-viral antibodies of interest.

7. The computer-implemented method of claim 6, wherein adjusting the received data comprises dividing the data representing the presence of labeled reagent in microparticles comprising the viral antigen bound to the viral group-reactive antibody and the anti-viral antibodies of interest by the data representing the presence of labeled reagent in microparticles pretreated with the negative control antigen to determine adjusted data.

8. The computer-implemented method of claim 7, wherein normalizing the received data comprises:
dividing the data representing the presence of labeled reagent in microparticles comprising a first viral antigen bound to the viral group-reactive antibody and a first positive control antibody by data representing the presence of labeled reagent in microparticles comprising a second viral antigen bound to the viral group-reactive antibody and a second positive control antibody to determine a normalizing factor; and
multiplying the adjusted data by the normalizing factor.

9. The computer-implemented method of claim 8, wherein calibrating the received data comprises:
comparing the positive and negative control data for each antigen to corresponding averaged data of multiple plates via inverse linear regression to determine relationships.

10. The computer-implemented method of claim 9, wherein classifying the data comprises:
determining logarithmic transformations of the calibrated data;
subjecting the logarithmic transformations of the calibrated data to quadratic discriminant analysis to determine a discrimination rule for determining whether the data represents the presence or absence of the anti-viral antibodies of interest in the sample.

11. The computer-implemented method of claim 10, further comprising presenting the logarithmic transformations of the calibrated data on a plot wherein the logarithmic transformations for each antigen are plotted against one another with the discrimination rule as a visual representation of the presence or absence of anti-viral antibodies of interest in the sample.

12. The computer-implemented method of claim 10, further comprising presenting the logarithmic transformations of the calibrated data as a classification probability surface, wherein three dimensional plots of the data represent the classification probabilities computed on a grid over a range of data, and wherein a bottom of a trough on the classification surface is the discrimination rule.

13. The computer-implemented method of claim 10, further comprising determining non-specific reactivity of the antibodies to improve accuracy of the determination of whether the data represents the presence or absence of the anti-viral antibodies of interest in the sample.

14. The computer-implemented method of claim 1, wherein the at least one characteristic classification parameter that distinguishes microparticles comprises a particle fluorescence emission intensity parameter.

15. The computer-implemented method of claim 1, wherein the at least one characteristic classification parameter that distinguishes microparticles comprises a particle color parameter.

16. The computer-implemented method of claim 1, wherein the at least one characteristic classification parameter that distinguishes microparticles comprises a particle size parameter.

17. The computer-implemented method of claim 5, wherein the data indicating the presence of labeled reagent in microparticles pretreated with a negative control antigen are for control purposes.

18. The computer-implemented method of claim 5, wherein:
the negative control antigen is nonspecifically reactive with the anti-viral antibodies of interest.

19. The computer-implemented method of claim 18 wherein:
the data indicating the presence of labeled reagent in microparticles pretreated with a negative control antigen indicate nonspecific binding to the negative control antigen.

20. The computer-implemented method of claim 18 wherein:
the data indicating the presence of labeled reagent in microparticles pretreated with a negative control antigen indicate nonspecific binding to the negative control antigen or background noise.

21. The computer-implemented method of claim 5, wherein the data indicating the presence of labeled reagent in microparticles pretreated with a negative control antigen indicate background noise.

22. The computer-implemented method of claim 1, wherein the viral group-reactive antibody is a monoclonal antibody that specifically binds arbovirus antigens and comprises MAb 6B6C-1, dengue 4G2, or Murray Valley 4A1B-9.

23. The computer-implemented method of claim 1, wherein:
the microparticles comprise a pooled population of subsets of microparticles;
the microparticles in the pooled population have the viral group-reactive antibody;
and the microparticles in each of the subsets have (i) the at least one characteristic classification parameter that distinguishes one subset from those of another subset and (ii) a specific antigen reactive with both the viral group-reactive antibody and the anti-viral antibodies of interest.

24. The computer-implemented method of claim 23, wherein the at least one characteristic classification parameter that distinguishes one subset from those of another subset comprises at least one parameter selected from the group consisting of:
ratio of two dyes internal to microparticles;
particle fluorescence emission intensity;
particle color; and
particle size.

25. The computer-implemented method of claim 23 wherein the specific antigen is an arbovirus antigen.

26. The computer-implemented method of claim 23, wherein the viral group-reactive antibody is a monoclonal antibody and comprises MAb 6B6C-1, dengue 4G2, or Murray Valley 4A1B-9.

27. The computer-implemented method of claim 23, wherein the viral group-reactive antibody is a monoclonal antibody and comprises EEE 1A4B-6 or WEE 2A2C-3.

28. The computer-implemented method of claim 23, wherein the viral group-reactive antibody is a monoclonal antibody and comprises LAC 10G5.4.

29. The computer-implemented method of claim 1, wherein the microparticles comprise:
a first subset of the microparticles comprising a first reactive microparticle type comprising a first specific viral antigen reactive with the viral group-reactive antibody and reactive with a first specific anti-viral antibody of interest in the sample; and
a second subset of the set of microparticles comprising a second reactive microparticle type comprising a second specific viral antigen reactive with the viral group-reactive antibody and reactive with a second specific anti-viral antibody of interest in the sample.

30. The computer-implemented method of claim 29 wherein:
the microparticles comprise at least two types of microparticles with one type used for each subset; and
each type of microparticle comprises at least one unique characteristic classification parameter.

31. The method of claim 30, wherein the at least one unique characteristic classification parameter comprises at least one characteristic selected from the group consisting of:
ratio of two dyes internal to microparticles;
microparticle fluorescence emission;
microparticle size; and
microparticle color.

32. The computer-implemented method of claim 1, wherein the sample comprises human serum.

33. One or more computer-readable storage media having computer executable instructions for performing a method for determining presence or absence of anti-viral antibodies of interest in a sample, comprising:
receiving data indicating at least one characteristic classification parameter that distinguishes microparticles each having bound thereto a viral group-reactive antibody from other microparticles each having bound thereto the viral group-reactive antibody, wherein the viral group-reactive antibody is reactive to a plurality of viruses within a virus group;
classifying microparticles based on the at least one characteristic classification parameter;
receiving data, in a flow instrument, indicating presence or absence of a labeled reagent associated with the classified microparticles, wherein the labeled reagent is bound to the anti-viral antibodies of interest; and
determining presence or absence of anti-viral antibodies of interest based on the data indicating the presence or absence of the labeled reagent associated with the classified microparticles;
wherein the at least one characteristic classification parameter that distinguishes microparticles comprises a particle fluorescence emission intensity parameter;
wherein the received data indicating the presence or absence of the labeled reagent associated with the classified microparticles comprises (a)-(c):
(a) data indicating the presence of labeled reagent in microparticles comprising a viral antigen bound to the viral group-reactive antibody and the anti-viral antibodies of interest;
(b) data indicating the presence of labeled reagent in microparticles pretreated with a negative control antigen; and
(c) data indicating the presence of labeled reagent in microparticles comprising a viral antigen bound to the viral group-reactive antibody and a positive control antibody;
wherein determining the presence or absence of anti-viral antibodies of interest based on the data indicating the presence or absence of the labeled reagent associated with the classified microparticles comprises (d)-(g):
(d) adjusting the received data to account for antigen reactions;
(e) normalizing the received data to account for positive control reactions;
(f) calibrating the received data to standardize across multiple plates; and
(g) classifying the data to represent the presence or absence of the anti-viral antibodies of interest;
wherein adjusting the received data comprises dividing the data representing the presence of labeled reagent in microparticles comprising the viral antigen bound to the viral group-reactive antibody and the anti-viral antibodies of interest by the data representing the presence of labeled reagent in microparticles pretreated with the negative control antigen to determine adjusted data;
wherein normalizing the received data comprises (h)-(i):
(h) dividing the data representing the presence of labeled reagent in microparticles comprising a first viral antigen bound to the viral group-reactive antibody and a first positive control antibody by data representing the presence of labeled reagent in microparticles comprising a second viral antigen bound to the viral group-reactive antibody and a second positive control antibody to determine a normalizing factor; and
(i) multiplying the adjusted data by the normalizing factor;

wherein calibrating the received data comprises comparing the positive and negative control data for each antigen to corresponding averaged data of multiple plates via inverse linear regression to determine relationships;

wherein classifying the data comprises (j)-(k):

(j) determining logarithmic transformations of the calibrated data; and (k) subjecting the logarithmic transformations of the calibrated data to a discrimination rule determined using quadratic discriminant analysis for determining whether the data represents the presence or absence of anti-viral antibodies of interest in the sample;

wherein the method further comprises presenting the logarithmic transformations of the calibrated data as a classification probability surface, wherein three dimensional plots of the data represent the classification probabilities computed on a grid over a range of data, and wherein a bottom of a trough on the classification surface is the discrimination rule;

verifying, in a quality control step, that the received positive and negative control data is consistent with positive and negative control data for each antigen to corresponding averaged data of multiple plates; and determining nonspecific reactors to further classify the received classified data indicating presence or absence of a labeled reagent associated with the classified microparticles to determine the presence or absence of anti-viral antibodies of interest;

wherein the negative control antigen is nonspecifically reactive with the anti-viral antibodies of interest;

wherein the viral group-reactive antibody is a monoclonal antibody that specifically binds arbovirus antigens and comprises MAb 6B6C-1.

34. The method of claim 25, wherein the first specific viral antigen is a St. Louis encephalitis viral antigen and the second specific viral antigen is a West Nile virus antigen.

35. The computer-implemented method of claim 1, wherein the anti-viral antibodies of interest comprise antibodies from flavivirus, alphavirus, or bunyavirus.

36. The computer-implemented method of claim 1, wherein the first specific viral antigen is a St. Louis encephalitis viral antigen and the second specific viral antigen is a West Nile virus antigen.

37. The computer-implemented method of claim 1, wherein the virus group is flavivirus.

38. The computer-implemented method of claim 37, wherein the plurality of viruses flaviviruses-comprise West Nile virus, St. Louis encephalitis virus, Dengue virus, Murray Valley encephalitis virus, and Japanese encephalitis virus.

39. The computer-implemented method of claim 1, wherein the virus group is alphavirus.

40. The computer-implemented method of claim 39, wherein the plurality of viruses comprise Venezuelan equine encephalitis virus, Eastern equine encephalitis virus, Chikungunya virus, and Western equine encephalitis virus.

41. The computer-implemented method of claim 1, wherein the virus group is bunyavirus.

42. The computer-implemented method of claim 41, wherein the plurality of viruses comprise La Crosse encephalitis virus and Jamestown Canyon virus.

43. A computer-implemented method for determining presence or absence of anti-viral group antibodies of interest in a sample comprising:

receiving data indicating at least one characteristic classification parameter that distinguishes microparticles having a viral group-reactive antibody from other microparticles having the viral group-reactive antibody;

classifying microparticles based on at least one characteristic classification parameter;

receiving data in a flow instrument indicating presence or absence of a labeled reagent associated with the classified microparticles, wherein the labeled reagent is bound to the anti-viral antibodies of interest, wherein the data received in the flow instrument is obtained by using a set of microparticles to which a viral group-reactive antibody is covalently bound, wherein the viral group-reactive antibody is reactive to a plurality of viruses within a virus group, wherein a subset of the viral group-reactive antibody is bound to a first specific viral antigen and a subset of the viral group-reactive antibody is bound to a second specific viral antigen, wherein the set of microparticles is combined with a sample comprising antibodies, and wherein a labeled reagent detects binding of anti-viral antibodies of interest from the sample to the first specific viral antigen or the second specific viral antigen;

wherein the received data indicating the presence or absence of the labeled reagent associated with the classified microparticles comprises:

data indicating the presence of labeled reagent in microparticles comprising a viral antigen bound to the viral group-reactive antibody and the anti-viral antibodies of interest;

data indicating the presence of labeled reagent in microparticles pretreated with a negative control antigen, wherein the negative control antigen is nonspecifically reactive with the anti-viral antibodies of interest; and data indicating the presence of labeled reagent in microparticles comprising a viral antigen bound to the viral group-reactive antibody and a positive control antibody; and determining presence or absence of anti-viral antibodies of interest in the sample based on the data indicating the presence or absence of the labeled reagent associated with the classified microparticles, wherein the method is performed on a suitably programmed computer.

* * * * *

UNITED STATES PATENT AND TRADEMARK OFFICE
CERTIFICATE OF CORRECTION

PATENT NO. : 7,933,721 B2
APPLICATION NO. : 11/336639
DATED : April 26, 2011
INVENTOR(S) : Basile et al.

It is certified that error appears in the above-identified patent and that said Letters Patent is hereby corrected as shown below:

On the Cover Page:

(75) Inventor "Alison Jane Johnson" should be --Alison Jane Basile--.

In the Specification:

Column 14, lines 48-49 "$MFI_{viral\ antigen\ 1}/MFI_{negative\ control\ antigen\ 1} = Adj\ MFI_{antigen\ 1}$" should be --$MFI_{viral\ antigen\ 1}/MFI_{negative\ control\ antigen\ 1} = Adj\ MFI_{antigen\ 1}$--.

Column 36, line 57, "Include" should be --include--.

In the Claims:

Column 45, line 47, claim 38, "viruses flaviviruses-comprise" should be --viruses comprise--.

Signed and Sealed this
Twenty-fifth Day of October, 2011

David J. Kappos
*Director of the United States Patent and Trademark Office*